(12) United States Patent
Farquhar et al.

(10) Patent No.: US 11,896,628 B2
(45) Date of Patent: Feb. 13, 2024

(54) METHODS AND COMPOSITIONS FOR THE TREATMENT OF C. DIFFICILE

(71) Applicant: Artugen Therapeutics Ltd., Dublin (IE)

(72) Inventors: Ronald Farquhar, Boston, MA (US); Christopher K. Murphy, Dublin (IE); Colin Hill, Dublin (IE); Paul Ross, Dublin (IE); Mary Rea, Fermoy (IE); Michelle O'Donnell, Waterford (IE); Brian Healy, Mallow (IE); Laurent Chesnel, Bedford, MA (US)

(73) Assignee: Artugen Therapeutics Ltd., Dublin (IE)

( * ) Notice: Subject to any disclaimer, the term of this patent is extended or adjusted under 35 U.S.C. 154(b) by 0 days.

(21) Appl. No.: 17/856,013

(22) Filed: Jul. 1, 2022

(65) Prior Publication Data
US 2023/0132133 A1    Apr. 27, 2023

Related U.S. Application Data

(63) Continuation of application No. 15/734,747, filed as application No. PCT/US2019/035740 on Jun. 6, 2019, now Pat. No. 11,419,900.

(60) Provisional application No. 62/681,774, filed on Jun. 7, 2018.

(51) Int. Cl.
| | |
|---|---|
| *A61K 35/74* | (2015.01) |
| *A61P 1/12* | (2006.01) |
| *A61K 9/19* | (2006.01) |
| *A61K 45/06* | (2006.01) |
| *A61K 47/36* | (2006.01) |

(52) U.S. Cl.
CPC ............... *A61K 35/74* (2013.01); *A61K 9/19* (2013.01); *A61K 45/06* (2013.01); *A61K 47/36* (2013.01); *A61P 1/12* (2018.01)

(58) Field of Classification Search
None
See application file for complete search history.

(56) References Cited

U.S. PATENT DOCUMENTS

| | | |
|---|---|---|
| 2008/0005747 A1 | 1/2008 | Meyer et al. |
| 2008/0057047 A1 | 3/2008 | Sas et al. |
| 2015/0147303 A1 | 5/2015 | Hsieh |
| 2015/0257400 A1 | 9/2015 | Reuter et al. |
| 2017/0224745 A1 | 8/2017 | Dart |
| 2017/0246222 A1 | 8/2017 | Lewis et al. |
| 2021/0220411 A1 | 7/2021 | Farquhar et al. |

FOREIGN PATENT DOCUMENTS

| | | |
|---|---|---|
| CN | 104974950 | 10/2015 |
| JP | 2009-519238 A | 5/2009 |
| JP | 2016-116466 | 6/2016 |
| KR | 10-2016-0141267 | 12/2016 |
| KR | 20160141267 | 12/2016 |
| RU | 2509148 | 3/2014 |
| WO | WO-2007/064741 | 6/2007 |
| WO | WO-2013/153159 | 10/2013 |
| WO | WO-2016/011511 | 1/2016 |
| WO | WO-2016/060934 | 4/2016 |
| WO | WO-2016/118864 A1 | 7/2016 |
| WO | WO-2019/175782 | 9/2019 |
| WO | WO-2021/116983 | 6/2021 |

OTHER PUBLICATIONS

"Artugen Therapeutics Announces First Patient Dosed with ART24", Artugen Therapeutics, Mar. 12, 2020, Retreived on Oct. 5, 2021 from https://artugentherapeutics.com/artugen-therapeutics-announces-first-patient-dosed-with-art24-artugens-first-clinical-product-candidate-for-prevention-of-recurrence-of-clostridium-difficile-infection/.

Geeraerts et al. "B acillus amyloliquefaciens as prophylactic treatment for Clostridium difficile-associated disease in a mouse model," Journal of Gastroenterology and Hepatology, Jul. 23, 2015, vol. 30, No. 8 pp. 1275-1280.

Geeraerts et al. "Use of Bacillus amyloliquefaciens for Clostridium perfringens and Clostridium difficile associated disease", Jan. 1, 2016, Retrieved on Oct. 20, 2020 from https://biblio.ugent.be/publication/8102182/file/8102183.pdf.

International Search Report and Written Opinion on International Patent Application No. PCT/US2019/035740 dated Oct. 10, 2019 (23 pages).

Lee et al., "Antimicrobial Activity of Bacillus amyloliquefaciens EMD17 Isolated from Cheonggukjang and Potential Use as a Starter for Fermented Soy Foods", Food Sci. Biotechnol., Apr. 30, 2016, vol. 25(2), pp. 525-532.

O'Donnell et al., "Safety characterization of ART24, a novel live biotherapeutic product in development for the prevention of GDI, by in silico and in vitro testing", Oct. 21, 2020, Retrieved from http://web.archive.org/web/20201021093437if_/https://artugentherapeutics.com/wpcontent/uploads/2020/04/artugen_1536.pdf.

Sim et al., "Antipathogenic Activity of Bacillus amyloliquefaciens Isolated from Korean Traditional Rice Wine", Korean Journal of Microbiology and Biotechnology, Mar. 28, 2016, vol. 44, No. 1, pp. 98-105.

*Primary Examiner* — Brian Gangle
(74) *Attorney, Agent, or Firm* — Foley & Lardner LLP

(57) ABSTRACT

Disclosed herein are compositions and methods for preventing, ameliorating, or treating *Clostridium difficile* infections and/or reducing the severity of one or more risk factors, signs, or symptoms associated with *C. difficile* infections. In particular, the technology of the present disclosure relates to methods for administering an effective amount of a composition comprising strains of *Bacillus amyloliquefaciens* bacteria identified as ART24, ART4, and ART 12, to a subject suffering from or at risk for *C. difficile* infections.

15 Claims, 26 Drawing Sheets

L.monocytogenes DPC1768

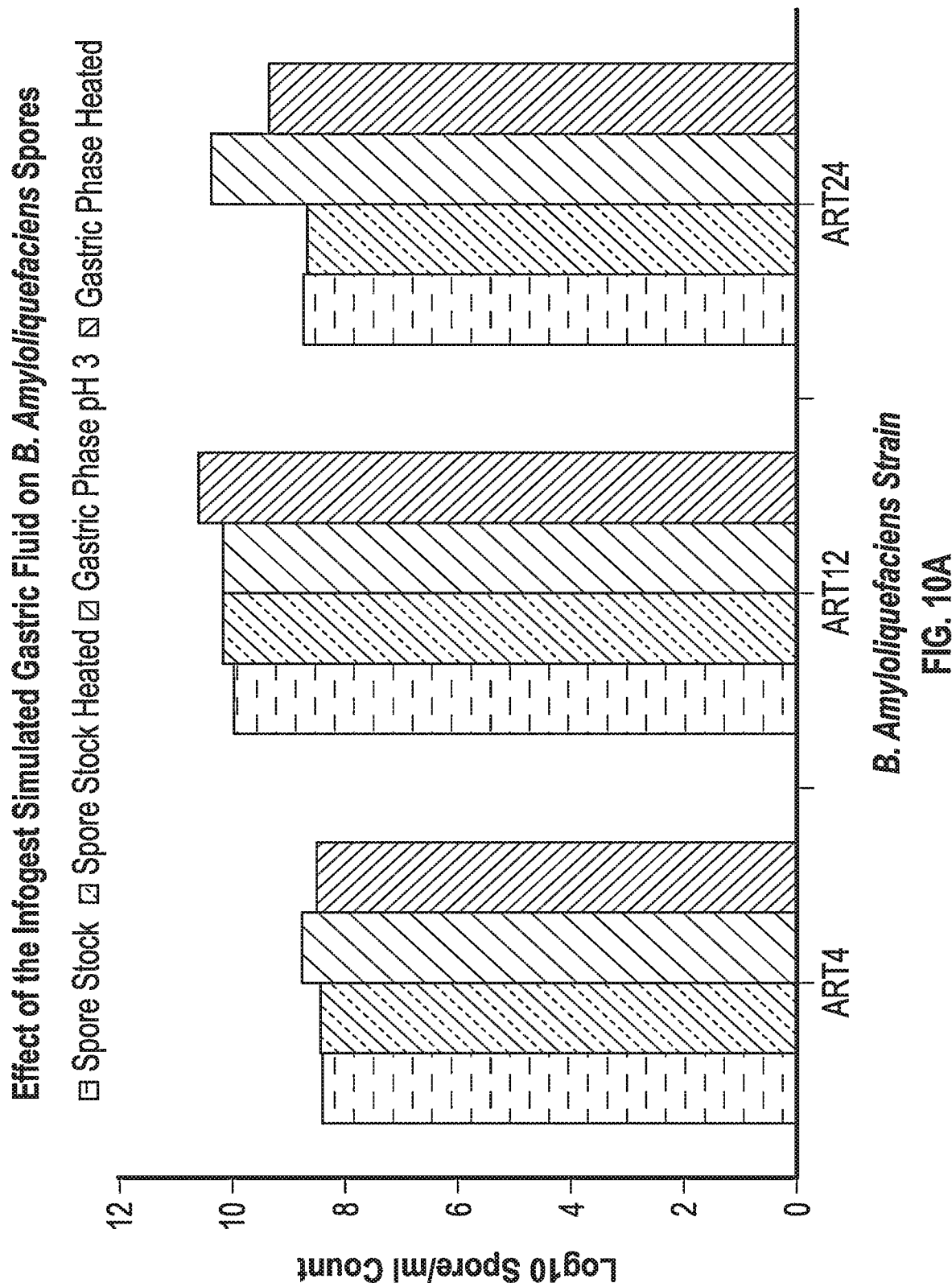

METHODS AND COMPOSITIONS FOR THE TREATMENT OF C. DIFFICILE

CROSS-REFERENCE TO RELATED APPLICATION

The present application is a continuation of U.S. patent application Ser. No. 15/734,747 filed Dec. 3, 2020, now U.S. Pat. No. 11,419,900 issued Aug. 23, 2022, which is a U.S. National Stage Application under 35 U.S.C. § 371 of International Patent Application No. PCT/US2019/035740, filed on Jun. 6, 2019, which claims the benefit of and priority to U.S. Provisional Patent Application No. 62/681,774, filed on Jun. 7, 2018, the contents of which are incorporated herein by reference in their entireties.

TECHNICAL FIELD

The present technology relates generally to methods and compositions for preventing, ameliorating, or treating *Clostridium difficile* infections and/or reducing the severity of one or more risk factors, signs, or symptoms associated with *C. difficile* infections. In particular, the present technology relates to administering an effective amount of a composition comprising strains of *Bacillus amyloliquefaciens* bacteria identified as ART24, ART4, and ART12, to a subject suffering from or at risk for *C. difficile* infections.

BACKGROUND

The following description is provided to assist the understanding of the reader. None of the information provided or references cited is admitted to be prior art to the compositions and methods disclosed herein.

*Clostridium difficile* is a spore-forming, Gram-positive, anaerobic *bacillus* that can colonize the large bowel. Upon particular clinical conditions, e.g. when the natural microbiota has been disrupted or depleted, *C. difficile* can overgrow and produce toxins that cause disease pathologies. *C. difficile* infection (CDI) can cause symptoms ranging from mild diarrhea to life-threatening pseudomembranous colitis and toxic megacolon. The prolonged use of antibiotics, especially broad-spectrum agents, can induce a change in the composition and function of the intestinal microbiota resulting in antibiotic associated diarrhea (AAD). CDI or *Clostridium difficile*-associated disease (CDAD) is used to describe a constellation of illnesses caused by toxins A and B produced by the *C. difficile* bacillus.

*C. difficile* is the most common cause of nosocomial infectious diarrhea and is becoming an increasing burden to the health care system, resulting in approximately 29,000 deaths and totaling more than $1 billion per year in the United States. The emergence of highly virulent strains of *C. difficile* has been linked to increased disease prevalence and severity as well as higher rates of treatment failure with metronidazole.

Current therapeutic approaches involve terminating treatment with the offending antibiotic(s) and initiating treatment with vancomycin or metronidazole or fidaxomicin. Treatment of patients with *C. difficile* infection with Standard of Care (SOC) antibiotics reduces morbidity and mortality. However, the number of patients who do not respond to metronidazole is increasing. Antibiotic treatments will disrupt and can inhibit reestablishment of the beneficial endogenous gastrointestinal tract (GIT) microbiota, which renders the patients effectively cured to become at risk for recurrence of the disease. Despite advances in the treatment of infections, CDI recurrence is seen in about 10-35% of patients after their initial case of CDI, and in 35-65% of patients after a primary recurrence. Accordingly, there is a need for more effective therapies for CDI, and, in particular, therapies that preserve the endogenous gastrointestinal microbiota.

SUMMARY

In one aspect, the present disclosure provides a bacterial strain selected from the group consisting of ART24 (NCIMB Accession No. 43088), ART4 (NCIMB Accession No. 43086), and ART12 (NCIMB Accession No. 43087). In one aspect, the present disclosure provides a composition comprising one or more bacterial strains selected from the group consisting of ART24 (NCIMB Accession No. 43088), ART4 (NCIMB Accession No. 43086), and ART12 (NCIMB Accession No. 43087), and a preservative. In some embodiments, the bacterial strain is ART24 (NCIMB Accession No. 43088). In some embodiments, the bacterial strain is ART4 (NCIMB Accession No. 43086). In some embodiments, the bacterial strain is ART12 (NCIMB Accession No. 43087).

In some embodiments, the bacterial strain is lyophilized. In some embodiments, the bacterial strain is in the form of a spore. In some embodiments, the preservative is selected from the group consisting of sucrose, trehalose, sodium ascorbate, and glutathione. In some embodiments, the preservative is a cyroprotectant. In some embodiments, the cryoprotectant is selected from the group consisting of a nucleotide, a disaccharide, a polyol, and a polysaccharide. In some embodiments, the cryoprotectant is selected from the group consisting of inosine-5'-monophosphate (IMP), guanosine-5'-monophosphate (GMP), adenosine-5'-monophosphate (AMP), uranosine-5'-monophosphate (UMP), cytidine-5'-monophosphate (CMP), adenine, guanine, uracil, cytosine, guanosine, uridine, cytidine, hypoxanthine, xanthine, orotidine, thymidine, inosine, trehalose, maltose, lactose, sucrose, sorbitol, mannitol, dextrin, inulin, sodium ascorbate, glutathione, skim milk, and cryoprotectant 18. In some embodiments, the cryoprotectant comprises trehalose.

In one aspect, the present disclosure provides a pharmaceutical composition comprising one or more bacterial strains selected from the group consisting of ART24 (NCIMB Accession No. 43088), ART4 (NCIMB Accession No. 43086), and ART12 (NCIMB Accession No. 43087), and a pharmaceutically acceptable carrier. In some embodiments, the pharmaceutically acceptable carrier comprises a polysaccharide, locust bean gum, an anionic polysaccharide, a starch, a protein, sodium ascorbate, glutathione, trehalose, sucrose, or pectin. In some embodiments, the polysaccharide comprises a plant, animal, algal, or microbial polysaccharide. In some embodiments, the polysaccharide comprises guar gum, inulin, amylose, chitosan, chondroitin sulphate, an alginate, or dextran. In some embodiments, the starch comprises rice starch.

In some embodiments, the composition further comprises an antibiotic. In some embodiments, the antibiotic comprises one or more of metronidazole, vancomycin, and nitazoxanide.

In some embodiments, the composition is formulated for enteric administration. In some embodiments, the composition is formulated for oral delivery, for sublingual delivery, for rectal delivery, or for use as a probiotic.

In one aspect, the present disclosure provides a method for treating or preventing a *Clostridium difficile* infection or a *Clostridium difficile*-associated disease (CDAD) in a subject in need thereof, the method comprising administering to the subject a therapeutically effective amount of a pharmaceutical composition comprising one or more bacterial strains selected from the group consisting of ART24 (NCIMB Accession No. 43088), ART4 (NCIMB Accession No. 43086), and ART12 (NCIMB Accession No. 43087). In some embodiments, the bacterial strain is ART24 (NCIMB Accession No. 43088). In some embodiments, the bacterial strain is ART4 (NCIMB Accession No. 43086). In some embodiments, the bacterial strain is ART12 (NCIMB Accession No. 43087).

In some embodiments, the bacterial strain is lyophilized. In some embodiments, the bacterial strain is in the form of a spore.

In some embodiments, the C. difficile infection or CDAD comprise one or more of diarrhea, weight loss, appetite loss, bloating, flu-like symptoms, fever, abdominal pain, nausea, dehydration, colitis, and pseudomembraneous colitis. In some embodiments, the CDAD comprises antibiotic-associated diarrhea (AAD).

In some embodiments, the pharmaceutical composition is administered enterally. In some embodiments, the method further comprises separately, sequentially, or simultaneously administering one or more antibiotics to the subject. In some embodiments, the one or more antibiotics comprises one or more of metronidazole, vancomycin, and nitazoxanide. In some embodiments, the method further comprises separately, sequentially, or simultaneously administering an anti-toxin B monoclonal antibody.

In one aspect, the present disclosure provides a use of a composition in the preparation of a medicament for treating or preventing a Clostridium difficile infection or a Clostridium difficile-associated disease (CDAD) in a subject in need thereof, wherein the composition comprises one or more bacterial strains selected from the group consisting of ART24 (NCIMB Accession No. 43088), ART4 (NCIMB Accession No. 43086), and ART12 (NCIMB Accession No. 43087). In some embodiments, the bacterial strain is ART24 (NCIMB Accession No. 43088). In some embodiments, the bacterial strain is ART4 (NCIMB Accession No. 43086). In some embodiments, the bacterial strain is ART12 (NCIMB Accession No. 43087).

In some embodiments, the bacterial strain is lyophilized. In some embodiments, the bacterial strain is in the form of a spore.

In some embodiments, the C. difficile infection or CDAD comprise one or more of diarrhea, weight loss, appetite loss, bloating, flu-like symptoms, fever, abdominal pain, nausea, dehydration, colitis, and pseudomembraneous colitis. In some embodiments, the CDAD comprises antibiotic-associated diarrhea (AAD).

In some embodiments, the medicament is formulated to be administered orally, sublingually, or rectally. In some embodiments, treating or preventing comprises separately, sequentially, or simultaneously administering one or more antibiotics to the subject. In some embodiments, the one or more antibiotics comprises one or more of metronidazole, vancomycin, and nitazoxanide. In some embodiments, treating or preventing comprises separately, sequentially, or simultaneously administering an anti-toxin B monoclonal antibody.

In one aspect, the present disclosure provides a method for treating or preventing a Clostridium perfringens infection in a subject in need thereof, the method comprising administering to the subject a therapeutically effective amount of a pharmaceutical composition comprising a bacterial strain selected from the group consisting of ART24 (NCIMB Accession No. 43088), ART4 (NCIMB Accession No. 43086), and ART12 (NCIMB Accession No. 43087). In some embodiments, the bacterial strain is ART24 (NCIMB Accession No. 43088). In some embodiments, the bacterial strain is ART4 (NCIMB Accession No. 43086). In some embodiments, the bacterial strain is ART12 (NCIMB Accession No. 43087).

In some embodiments, the bacterial strain is lyophilized. In some embodiments, the bacterial strain is in the form of a spore.

In some embodiments, the infection comprises one or more of abdominal pain, stomach cramps, diarrhea, and nausea. In some embodiments, the pharmaceutical composition is administered enterally. In some embodiments, the method further comprises separately, sequentially, or simultaneously administering one or more antibiotics to the subject. In some embodiments, the one or more antibiotics comprises one or more of metronidazole, vancomycin, and nitazoxanide.

In one aspect, the present disclosure provides a use of a composition in the preparation of a medicament for treating or preventing a Clostridium perfringens infection in a subject in need thereof, wherein the composition comprises one or more bacterial strains selected from the group consisting of ART24 (NCIMB Accession No. 43088), ART4 (NCIMB Accession No. 43086), and ART12 (NCIMB Accession No. 43087). In some embodiments, the bacterial strain is ART24 (NCIMB Accession No. 43088). In some embodiments, the bacterial strain is ART4 (NCIMB Accession No. 43086). In some embodiments, the bacterial strain is ART12 (NCIMB Accession No. 43087).

In some embodiments, the bacterial strain is lyophilized. In some embodiments, the bacterial strain is in the form of a spore.

In some embodiments, the infection comprises one or more of abdominal pain, stomach cramps, diarrhea, and nausea. In some embodiments, the pharmaceutical composition is administered enterally. In some embodiments, the use further comprises separately, sequentially, or simultaneously administering one or more antibiotics to the subject. In some embodiments, the one or more antibiotics comprises one or more of metronidazole, vancomycin, and nitazoxanide.

In one aspect, the present disclosure provides a method for treating or preventing a Listeria monocytogenes infection in a subject in need thereof, the method comprising administering to the subject a therapeutically effective amount of a pharmaceutical composition comprising one or more bacterial strains selected from the group consisting of ART24 (NCIMB Accession No. 43088), ART4 (NCIMB Accession No. 43086), and ART12 (NCIMB Accession No. 43087). In some embodiments, the bacterial strain is ART24 (NCIMB Accession No. 43088). In some embodiments, the bacterial strain is ART4 (NCIMB Accession No. 43086). In some embodiments, the bacterial strain is ART12 (NCIMB Accession No. 43087).

In some embodiments, the bacterial strain is lyophilized. In some embodiments, the bacterial strain is in the form of a spore.

In some embodiments, the infection comprises one or more of abdominal pain, flu like symptoms, stomach cramps, diarrhea, and nausea. In some embodiments, the pharmaceutical composition is administered enterally. In some embodiments, the method further comprises separately, sequentially, or simultaneously administering one or more antibiotics to the subject. In some embodiments, the one or more antibiotics comprises one or more of metronidazole, vancomycin, and nitazoxanide.

In one aspect, the present disclosure provides a use of a composition in the preparation of a medicament for treating or preventing a *Listeria monocytogenes* infection in a subject in need thereof, wherein the composition comprises one or more bacterial strains selected from the group consisting of ART24 (NCIMB Accession No. 43088), ART4 (NCIMB Accession No. 43086), and ART12 (NCIMB Accession No. 43087). In some embodiments, the bacterial strain is ART24 (NCIMB Accession No. 43088). In some embodiments, the bacterial strain is ART4 (NCIMB Accession No. 43086). In some embodiments, the bacterial strain is ART12 (NCIMB Accession No. 43087).

In some embodiments, the bacterial strain is lyophilized. In some embodiments, the bacterial strain is in the form of a spore.

In some embodiments, the infection comprises one or more of abdominal pain, flu like symptoms, stomach cramps, diarrhea, and nausea. In some embodiments, the pharmaceutical composition is administered enterally. In some embodiments, the use further comprises separately, sequentially, or simultaneously administering one or more antibiotics to the subject. In some embodiments, the one or more antibiotics comprises one or more of metronidazole, vancomycin, and nitazoxanide.

In one aspect, the present disclosure provides a method for treating or preventing a *Vibrio parahaemolyticus* infection in a subject in need thereof, the method comprising administering to the subject a therapeutically effective amount of a pharmaceutical composition comprising one or more bacterial strains selected from the group consisting of ART24 (NCIMB Accession No. 43088), ART4 (NCIMB Accession No. 43086), and ART12 (NCIMB Accession No. 43087). In some embodiments, the bacterial strain is ART24 (NCIMB Accession No. 43088). In some embodiments, the bacterial strain is ART4 (NCIMB Accession No. 43086). In some embodiments, the bacterial strain is ART12 (NCIMB Accession No. 43087).

In some embodiments, the bacterial strain is lyophilized. In some embodiments, the bacterial strain is in the form of a spore.

In some embodiments, the subject is a fish or crustacean. In some embodiments, the fish or crustacean is in an aquaculture environment. In some embodiments, the administering comprises providing the composition to the aquaculture environment. In some embodiments, the composition is formulated as a fish feed or fish feed additive. In some embodiments, the composition is formulated as a bath treatment agent. In some embodiments, the pharmaceutical composition is administered enterally.

In some embodiments, the method further comprises separately, sequentially, or simultaneously administering one or more antibiotics to the subject. In some embodiments, the one or more antibiotics comprises one or more of metronidazole, vancomycin, and nitazoxanide.

In one aspect, the present disclosure provides a use of a composition in the preparation of a medicament for treating or preventing a *Vibrio parahaemolyticus* infection in a subject in need thereof, wherein the composition comprises one or more bacterial strains selected from the group consisting of ART24 (NCIMB Accession No. 43088), ART4 (NCIMB Accession No. 43086), and ART12 (NCIMB Accession No. 43087). In some embodiments, the bacterial strain is ART24 (NCIMB Accession No. 43088). In some embodiments, the bacterial strain is ART4 (NCIMB Accession No. 43086). In some embodiments, the bacterial strain is ART12 (NCIMB Accession No. 43087).

In some embodiments, the bacterial strain is lyophilized. In some embodiments, the bacterial strain is in the form of a spore.

In some embodiments, the subject is a fish or crustacean. In some embodiments, the fish or crustacean is in an aquaculture environment. In some embodiments, the administering comprises providing the composition to the aquaculture environment. In some embodiments, the composition is formulated as a fish feed or fish feed additive. In some embodiments, the composition is formulated as a bath treatment agent.

In some embodiments, the pharmaceutical composition is administered enterally. In some embodiments, the use further comprises separately, sequentially, or simultaneously administering one or more antibiotics to the subject. In some embodiments, the one or more antibiotics comprises one or more of metronidazole, vancomycin, and nitazoxanide.

BRIEF DESCRIPTION OF THE DRAWINGS

FIGS. 1A-1B are photographs showing the direct anti-*C. difficile* properties of culture supernatant of *B. amyloliquefaciens* strains ART12, ART24, and ART4. A well-diffusion assay shown in FIG. 1A shows large zones of anti-*C. difficile* activity for each of the culture supernatants from strains ART12, ART24, and ART4. FIG. 1B shows zones of anti-*C. difficile* activity from 24, 48, and 72 hours culture supernatants of strains ART4, ART12, and ART24.

FIGS. 2A-2B show well diffusion assays demonstrating that *B. amyloliquefaciens* strains of the present technology are resistant to digestive proteases. FIG. 2A shows that the anti-*C. difficile* activity of ART24 supernatant is resistant to inactivation by pepsin and trypsin. FIG. 2B shows that the anti-*C. difficile* activity of ART4 supernatant is resistant to inactivation by trypsin, chymotrypsin, and proteinase-K.

FIGS. 3A-3C are MALDI-TOF MS chromatographs of HPLC fractions of culture ART24 (FIG. 3A), ART4 (FIG. 3B), and DSM7T (FIG. 3C) culture supernatants. The spectra show that the anti-*C. difficile* bioactive fractions from ART24 (FIG. 3A) and ART4 (FIG. 3B) culture supernatants contain the anti-*C. difficile* compound amylocyclicin. As shown in FIG. 3D, amylocyclicin is not present on the spectrum from fractions of DSM7T culture supernatant.

FIG. 4A shows a well diffusion assay using *C. difficile* as the indicator, where proteinase-K (ProK) was added directly (center well) or adjacent (right-hand well) to a well containing ART24 culture supernatant. FIG. 4B is a set of MALDI-TOF MS chromatographs showing that ART24 anti-*C. difficile* activity is maintained even when the amylocyclicin peak is lost in the presence of ProK.

FIG. 5A is a chart showing the results of a 24-hour co-culture of ART24 and *C. difficile*. *C. difficile* growth is decreased greater than 2 log upon exposure to ART24. FIG. 5B is a chart showing inoculation of 10× ART24 into an ongoing *C. difficile* culture at T3h and T6h, for 24 hours results in a decrease in *C. difficile* growth per OD reading.

FIG. 6A shows a well diffusion assay demonstrating the activity of culture supernatant of ART4, ART12, and ART24 strains against several different *C. difficile* clinical isolates. FIG. 6B shows a well diffusion assay demonstrating the anti-*C. difficile* activity of culture supernatant of ART24 against 28 contemporary *C. difficile* clinical isolates.

FIG. 7A shows well diffusion assays for (top panel from left to right): *Lactobacillus reuteri, Lactobacillus rhamnosus, Staphylococcus capitis*; and (bottom panel from left to right): *Bacillus thuringiensis*, and *Clostridium difficile* comparing ART4 ("A4"), ART12 ("12 Aer 1"), and ART24

("024(2)") activities against each. The assay shows a comparison of 24h and 48h ART4, ART12, and ART24 culture supernatants. FIG. 7B is a chart showing a qPCR analysis. Fresh ART 24 strains added to in vitro human colonic microbiota samples spare the human colonic phyla investigated, namely proteobacteria, firmicutes, Bacteroidetes, verrucomicrobia, and lactobaccilus.

FIG. 8A shows an illustrative design for assessing the in vivo efficacy of the *B. amyloliquefaciens* (B. amy) strains of the present technology. FIG. 8B is a chart showing the percentage of *C. difficile* infected mice exhibiting abnormal clinical signs after daily treatment with ART24 vegetative cells resuspended in PBS ("B amy PBS"), ART24 vegetative cells resuspended in spent medium ("B amy QD"), vancomycin, or PBS ("vehicle"). FIG. 8C is a chart showing the percentage weight change from day 0 for each of the treatment groups. FIG. 8D is a chart showing the percentage weight change from day 0 of the "B. amy PBS" group and per day statistical analysis. *p<0.05; **p<0.01; 2-way ANOVA with multiple comparisons. FIG. 8E is a Kaplan-Meier survival curve showing the percent survival post-*C. difficile* infection in each of the treatment groups.

FIG. 9A shows well diffusion assays demonstrating the inhibitory effects of ART12, ART24, and ART4 against 7 clinical isolates of *C. perfringens*.

FIGS. 9B-9E are MALDI-TOF MS chromatographs of HPLC fractions of culture $DSM7^T$ (FIG. 9B), ART4 (FIG. 9C), ART12 and (FIG. 9D), ART24 (FIG. 9E) against *C. perfringens*. Mass spectra of active fractions indicate plipastatin (fengycin) as the active anti-*C. perfringens* metabolite. Plipastatin is not present on spectrum from fractions of $DSM7^T$ culture supernatant.

FIG. 10A is a chart showing the effect of simulated gastric fluid (pH 3) on *B. amyloliquefaciens* spores.

DETAILED DESCRIPTION

Figure 1A:
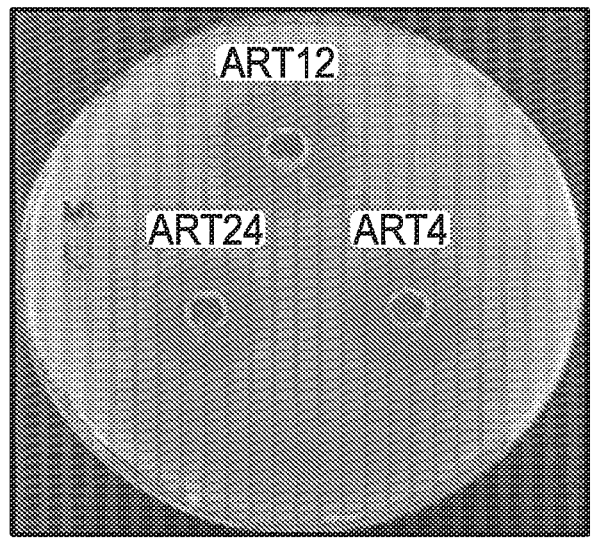

It is to be appreciated that certain aspects, modes, embodiments, variations and features of the present technology are described below in various levels of detail in order to provide a substantial understanding of the present technology. The definitions of certain terms as used in this specification are provided below. Unless defined otherwise, all technical and scientific terms used herein generally have the same meaning as commonly understood by one of ordinary skill in the art to which this present technology belongs.

I. Definitions

The following terms are used herein, the definitions of which are provided for guidance.

As used herein, the singular forms "a," "an," and "the" designate both the singular and the plural, unless expressly stated to designate the singular only.

The term "about" and the use of ranges in general, whether or not qualified by the term about, means that the number comprehended is not limited to the exact number set forth herein, and is intended to refer to ranges substantially within the quoted range while not departing from the scope of the invention. As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

As used herein, "administration" of an agent, drug, bacterial strain or spore thereof, or composition of the present technology to a subject includes any route of introducing or delivering to a subject a compound to perform its intended function. Administration can be carried out by any suitable route, including orally, intranasally, parenterally (intravenously, intramuscularly, intraperitoneally, or subcutaneously), topically, or by inhalation. In some embodiments, the compositions of the present technology are formulated for enteric administration. In some embodiments, the compositions are formulated for oral, sublingual, or rectal delivery. In some embodiments, the compositions are formulated for use as a probiotic. In some embodiments, the compositions are formulated for use as a live biotherapeutic. As used herein, administration includes self-administration and administration by another.

As used herein, "ART24" or "ART024(2)" or "024(2)" refers to a bacterial strain, or spore thereof, having been deposited under NCIMB Accession No. 43088, or compositions comprising the strain.

As used herein, "ART4" or "A4" refers to a bacterial strain, or spore thereof, having been deposited under NCIMB Accession No. 43086, or compositions comprising the strain.

As used herein, "ART12" or "12 Aer 1" refers to a bacterial strain, or spore thereof, having been deposited under NCIMB Accession No. 43087, or compositions comprising the strain.

As used herein, the terms "effective amount," or "therapeutically effective amount," and "pharmaceutically effective amount" refer to a quantity sufficient to achieve a desired therapeutic and/or prophylactic effect, e.g., an amount which results in the prevention of a disease, condition, and/or symptom(s) thereof. In the context of therapeutic or prophylactic applications, the amount of a composition administered to the subject will depend on the type and severity of the disease and on the characteristics of the subject, such as general health, age, sex, body weight, and tolerance to the composition drugs. It will also depend on the degree, severity, and type of disease or condition. The skilled artisan will be able to determine appropriate dosages depending on these and other factors. In some embodiments, multiple doses are administered. Additionally or alternatively, in some embodiments, multiple therapeutic compositions or compounds (e.g., pharmaceutical compositions comprising multiple bacterial strains alone or in combination with additional active agents, such as antibiotics or anti-toxin B monoclonal antibody) are administered. In the methods described herein, compositions comprising the bacterial strains of the present technology, or spores thereof, may be administered to a subject having one or more signs, symptoms, or risk factors of *C. difficile* infection (CDI) or *Clostridium difficile*-associated disease (CDAD), including, but not limited to diarrhea, weight loss, appetite loss, bloating, flu-like symptoms, fever, abdominal pain, nausea, dehydration, colitis, and pseudomembraneous colitis. For example, a "therapeutically effective amount" of the compositions of the present technology, includes levels at which the presence, frequency, or severity of one or more signs, symptoms, or risk factors of CDI or CDAD are, at a minimum, ameliorated. In some embodiments, a therapeutically effective amount reduces or ameliorates the physiological effects of CDI or CDAD, and/or the risk factors of CDI or CDAD, and/or the likelihood of developing CDI or CDAD. In some embodiments, a therapeutically effective amount is achieved by multiple administrations. In some embodiments, a therapeutically effective amount is achieved with a single administration.

As used herein, the terms "freeze-dried" or "freeze-drying" and "lyophilized" or "lyophilization" are used interchangeably and refer to a process that removes water from a product after it is frozen and placed under a vacuum and the products produced therefrom.

As used herein, "pharmaceutically acceptable carrier and/or diluent" or "pharmaceutically acceptable excipient" includes but is not limited to solvents, dispersion media, coatings, antibacterial and antifungal agents, isotonic and absorption delaying agents, and the like. In some embodiments, the pharmaceutically acceptable carrier comprises a polysaccharide, locust bean gum, an anionic polysaccharide, a starch, a protein, sodium ascorbate, glutathione, trehalose, sucrose, or pectin. In some embodiments, the polysaccharide comprises a plant, animal, algal, or microbial polysaccharide. In some embodiments, the polysaccharide comprises guar gum, inulin, amylose, chitosan, chondroitin sulphate, an alginate, or dextran. In some embodiments, the starch comprises rice starch. The use of such media and agents for biologically active substances is well known in the art. Further details of excipients are provided below. Supplementary active ingredients, such as antimicrobials, for example antifungal agents, can also be incorporated into the compositions.

As used herein, "pharmaceutically acceptable excipient" refers to substances and compositions that do not produce an adverse, allergic, or other untoward reaction when administered to an animal or a human. As used herein, the term includes all inert, non-toxic, liquid or solid fillers, or diluents that do not react with the therapeutic substance of the invention in an inappropriate negative manner, solvents, dispersion media, coatings, antibacterial and antifungal agents, isotonic and absorption delaying agents, preservatives and the like, for example liquid pharmaceutical carriers e.g., sterile water, saline, sugar solutions, Tris buffer, ethanol and/or certain oils.

As used herein, "probiotic" refers to bacteria comprising a component of the transient or endogenous flora of a subject administered to confer a beneficial prophylactic and/or therapeutic effect on the subject. Probiotics are generally known to be safe by those skilled in the art. Although not wishing to be bound by any particular mechanism, it is possible the prophylactic and/or therapeutic effect of a *B. amyloliquefaciens* strains of the present technology results from inhibition of pathogenic bacterial growth due to the production of extracellular products having antimicrobial activity. In some embodiments, "probiotics" include "live biotherapeutic products."

As used herein, "prevention," "prevent," or "preventing" of a disorder or condition refers to, in a statistical sample, reduction in the occurrence or recurrence of the disorder or condition in treated subjects/samples relative to an untreated controls, or refers delays the onset of one or more symptoms of the disorder or condition relative to the untreated controls.

As used herein "subject" and "patient" are used interchangeably. In some embodiments, the subject is an animal subject. In some embodiments, the animal subject is a mammal. In some embodiments, the mammalian subject is a human. In some embodiments, the animal subject is a fish or crustacean. In some embodiments, the fish or crustacean is in an aquaculture environment.

As used herein, the term "simultaneous" administration refers to the administration of at least two agents by the same route and at the same time or at substantially the same time.

As used herein, the term "separate" administration refers to an administration of at least two agents at the same time or at substantially the same time by different routes.

As used herein, the term "sequential" administration refers to administration of at least two agents at different times, the administration route being identical or different. More particularly, sequential use refers to the whole administration of one agent before administration of the other agent(s) commences. It is thus possible to administer one of the agents over several minutes, hours, or days before administering another.

A "synergistic therapeutic effect" refers to a greater-than-additive therapeutic effect which is produced by a combination of at least two therapeutic agents, and which exceeds that which would otherwise result from the individual administration of the agents. For example, use of bacterial strains of the present technology in conjunction with other agents for the treatment of CDI or CDAD may result in a greater than additive therapeutic effect. In some embodiments, the synergistic effect may permit the use of lower doses of bacterial strains of the present technology and/or other agents than would be required if each were used alone.

"Treating," "treat," "treated," or "treatment" of a disease or disorder includes: (i) inhibiting the disease or disorder, i.e., arresting its development; (ii) relieving the disease or disorder, i.e., causing its regression; (iii) slowing progression of the disorder; and/or (iv) inhibiting, relieving, or slowing progression of one or more symptoms of the disease or disorder.

It is to be appreciated that the various modes of treatment or prevention of medical diseases and conditions as described are intended to mean "substantial," which includes total but also less than total treatment or prevention, and wherein some biologically or medically relevant result is achieved.

II. *Clostridium difficile* Infection (CDI)

*Clostridium difficile* infection (CDI) or *Clostridium difficile*-associated disease (CDAD) is a symptomatic infection caused by the anaerobic, spore forming, Gram-positive bacterium, *Clostridium difficile*. Symptoms of CDI include watery diarrhea, fever, nausea, and abdominal pain. CDI underlies about 20% of cases of antibiotic-associated diarrhea (AAD). Complications of CDI may include pseudomembranous colitis, toxic megacolon, perforation of the colon, and sepsis and death.

CDI is transmitted by bacterial spores. The spores are resistant to many types of disinfectants, and may persist on contaminated surfaces, including food surfaces, for a period of months. Risk factors for CDI include antibiotic or proton pump inhibitor use, hospitalization, and advanced age. In healthy individuals, the growth of *C. difficile* is kept in check by normal microbiota present in the gastrointestinal tract. The use of broad-spectrum antibiotics and medications that decrease stomach acidity, such as proton pump inhibitors, can allow *C. difficile* bacteria to proliferate and promote infection. In the colon, *C. difficile* produces an enterotoxin (toxin A) and a cytotoxin (toxin B). The toxins stimulate the production of inflammatory mediators, which increase intestinal wall permeability leading to diarrhea, and cause degradation of colon epithelial cells. Diagnosis of CDI is by stool culture or testing for the presence of bacterial DNA or toxins.

In some embodiments, the present technology provides methods and compositions for the treating or preventing *C. difficile* infection, including reducing the severity of one or more risk factors, signs, or symptoms associated with *C. difficile* infections. In some embodiments the compositions comprise the novel *Bacillus amyloliquefaciens* strains ART24, ART4, and ART12, or spores thereof.

III. *Clostridium perfringens* Infection

*Clostridium perfringens* is a Gram-positive, anaerobic, spore-forming pathogenic bacterium ever-present in nature and found in soil, decaying vegetation, marine sediment, and the human gastrointestinal tract. *C. perfringens* is one of the most common causes of foodborne illness in the United States. Symptoms of *C. perfringens* infection may include abdominal pain, stomach cramps, diarrhea, and nausea. *C. perfringens* type c poisoning can lead to enteritis necroticans (also known as pigbel syndrome). This syndrome can cause death of intestinal cells and is often fatal.

In some embodiments, the present technology provides methods and compositions for the treating or preventing *C. perfringens* infection, including reducing the severity of one or more risk factors, signs, or symptoms associated with *C. perfringens* infections. In some embodiments the compositions comprise the novel *Bacillus amyloliquefaciens* strains ART24, ART4, and ART12, or spores thereof.

IV. *Listeria monocytogenes* Infection (Listeriosis)

*Listeria monocytogenes* is a Gram-positive, facultative anaerobic, pathogenic bacterium that grows and reproduces in host cells. Invasive infection by *L. monocytogenes* causes the disease listeriosis, is transmitted through the ingestion of contaminated food such as unpasteurized dairy or raw foods. *Listeria* can evade control in human foodstuffs due to its capacity to multiply and grow at refrigeration temperatures as low as 0° C., and is one of the most virulent foodborne pathogens. An estimated 1,600 people develop listeriosis each year in the United States, and about 260 deaths from the infection. The infection is most likely to sicken pregnant women and their newborns, adults aged 65 or older, and people with weakened immune systems. In high risk individuals, infection is fatal in 20-30% of cases. Infection may be limited to the gastrointestinal tract or may be invasive to the brain, spinal membranes, or bloodstream. In pregnant women, infection can lead to miscarriage, stillbirth, premature delivery of a life-threatening infection of the newborn.

In some embodiments, the present technology provides methods and compositions for the treating or preventing *L. monocytogenes* infection, including reducing the severity of one or more risk factors, signs, or symptoms associated with *L. monocytogenes* infections. In some embodiments the compositions comprise the novel *Bacillus amyloliquefaciens* strains ART24, ART4, and ART12, or spores thereof.

V. *Vibrio parahaemolyticus* Infection (Vibriosis)

*Vibrio parahaemolyticus* is an aquatic zoonotic agent that can threaten human and aquaculture animal health. *V. parahaemolyticus* is a Gram-negative, halophilic bacteria that is widespread and naturally present in marine and estuarine environments. Environmental factors influence their growth, and their numbers are highest when the water is warm. *V. parahaemolyticus* infections in humans are acquired through ingestion of contaminated seafood or through exposure of an open wound to seawater. *V. parahaemolyticus* has been associated with sporadic infections and outbreaks of gastroenteritis. *V. parahaemolyticus* is the leading causal agent of human acute gastroenteritis following the consumption of raw, undercooked, or mishandled marine products. Clinical features most often associated with *V. parahaemolyticus* infection include watery diarrhea, abdominal cramps, nausea, and vomiting; wound infections and septicemia occur less commonly. Laboratory diagnosis is made by isolation of the organism from clinical specimens, including blood, stool, and wound samples. Almost all cases of food-borne *V. parahaemolyticus* infection are associated with a recent history of seafood consumption. *V. parahaemolyticus* produces several toxins in human disease such as thermostable direct hemolysin (TDH), TDH-related haemolysin (TRH), and thermolabile hemolysin (TLH).

*V. parahaemolyticus* infection in aquaculture animals can result in significant economic losses. Infection is particularly damaging in shrimp cultures where vibriosis can lead to Acute Hepatopancreatic Necrosis Disease (AHPND) or Early Mortality Syndrome (EMS), and in salmon cultures where infection can cause hemorrhaging of the fins, eyes, and ventral surface with a very high mortality rate. Photorabdus insect-related (Pir) toxins consisting of PirA$^{vp}$ and PirB$^{vp}$ are the toxins associated with AHPND in shrimp. Antibiotic resistance has made the treatment of *V. parahaemolyticus* infection using antibiotics a challenge and there is a need to develop an alternative therapy to control *V. parahaemolyticus* infections in aquaculture.

In some embodiments, the present technology provides methods and compositions for the treating or preventing *V. parahaemolyticus* infection, including reducing the severity of one or more risk factors, signs, or symptoms associated with *V. parahaemolyticus* infections. In some embodiments the compositions comprise the novel *Bacillus amyloliquefaciens* strains ART24, ART4, and ART12, or spores thereof. In some embodiments, the present technology provides a bath (immersion) treatment agent comprising the novel *B. amyloliquefaciens* strains ART24, ART4, and ART12, or spores thereof for preventing or treating *V. parahaemolyticus* infections in aquaculture. In some embodiments, the present technology provides a fish feed or fish feed additive comprising the novel *B. amyloliquefaciens* strains ART24, ART4, and ART12, or spores thereof for preventing or treating *V. parahaemolyticus* infections in aquaculture.

VI. *Bacillus amyloliquefaciens* Strains of the Present Technology

The technology of the present disclosure relates to the discovery of several strains of *Bacillus amyloliquefaciens* bacteria, or spores thereof, effectively treating or preventing *C. difficile* infection. The bacterial strains were isolated from human stool samples and analyzed for anti-*C. difficile* activity. A primary screen was done for proteolytic activity, with a secondary screen for anti-*C. difficile* activity. Colonies showing antimicrobial activity against *C. difficile* strain were purified and designated as "ART24" (or "ART024(2)" or "024(2)"), "ART4" (or "A4"), and ART12 (or "12 Aer 1"). ART24 refers to a bacterial strain, or spore thereof, characterized by NCIMB Accession No. 43088, deposited at NCIMB Ltd., Ferguson Building, Craibstone Estate, Bucksburn, Aberdeen, AB21 9YA, Scotland, on 21 Jun. 2018, or compositions comprising the strain. ART4 refers to a bacterial strain, or spore thereof, characterized by NCIMB Accession No. 43086, deposited at NCIMB Ltd., Ferguson Building, Craibstone Estate, Bucksburn, Aberdeen, AB21 9YA, Scotland, on 21 Jun. 2018, or compositions comprising the strain. ART12 refers to a bacterial strain, or spore thereof, characterized by NCIMB Accession No. 43087, deposited at NCIMB Ltd., Ferguson Building, Craibstone Estate, Bucksburn, Aberdeen, AB21 9YA, Scotland, on 21 Jun. 2018, or compositions comprising the strain.

In some embodiments, bacterial strains of the present technology, or spores thereof, are used in methods and compositions for treating or preventing *C. difficile*, *C. perfringens*, or *L. monocytogenes* infections. In some embodiments, the bacterial strains comprise a probiotic for preventing or controlling *C. difficile*, *C. perfringens*, or *L. monocytogenes* infections. In some embodiments, compositions of the present technology comprise vegetative bacterial cells. In some embodiments, compositions of the present technology comprise bacterial spores. In some embodiments, compositions of the present technology comprise a combination of vegetative bacterial cells and bacterial spores.

VII. Therapeutic and Prophylactic Methods

The following discussion is presented by way of example only, and is not intended to be limiting.

One aspect of the present technology includes methods of treating or preventing *C. difficile* infection (CDI) in a subject diagnosed as having, suspected as having, or at risk of having CDI. In therapeutic applications, compositions or medicaments comprising a bacterial strain, or spore thereof, selected from the group consisting of ART24, ART4, ART12, and combinations thereof, are administered to a subject suspected of, or already suffering from such a disease (such as, e.g., subjects exhibiting diarrhea, weight loss, appetite loss, bloating, flu-like symptoms, fever, abdominal pain, nausea, dehydration, colitis, or pseudomembraneous colitis), in an amount sufficient to cure, or at least partially arrest, the symptoms of the disease, including its complications and intermediate pathological phenotypes in development of the disease.

Subjects suffering from CDI can be identified by any or a combination of diagnostic or prognostic assays known in the art. For example, typical symptoms of CDI include, but are not limited to diarrhea, weight loss, appetite loss, bloating, flu-like symptoms, fever, abdominal pain, nausea, dehydration, colitis, or pseudomembraneous colitis.

In some embodiments, CDI subjects treated with the bacterial strains of the present technology, or spores thereof, will show amelioration or elimination of one or more of the following symptoms: diarrhea, weight loss, appetite loss, bloating, flu-like symptoms, fever, abdominal pain, nausea, dehydration, colitis, or pseudomembraneous colitis.

In one aspect, the present technology provides a method for preventing or delaying the onset of CDI or symptoms of CDI in a subject at risk of having CDI. In some embodiments, the bacterial strains of the present technology are formulated as a probiotic useful as a food supplement and for re-establishing beneficial bacteria in the intestinal tract. In some embodiments, the bacterial strains of the present technology are formulated as a live biotherapeutic product useful in pharmaceutical applications.

One aspect of the present technology includes methods of treating or preventing *C. perfringens* infection in a subject diagnosed as having, suspected as having, or at risk of having *C. perfringens* infection. In therapeutic applications, compositions or medicaments comprising a bacterial strain, or spore thereof, selected from the group consisting of ART24, ART4, and ART12, are administered to a subject suspected of, or already suffering from such a disease (such as, e.g., subjects exhibiting diarrhea, weight loss, appetite loss, bloating, flu-like symptoms, fever, abdominal pain, nausea, dehydration, colitis, or pseudomembraneous colitis), in an amount sufficient to cure, or at least partially arrest, the symptoms of the disease, including its complications and intermediate pathological phenotypes in development of the disease.

Subjects suffering from *C. perfringens* infection can be identified by any or a combination of diagnostic or prognostic assays known in the art. For example, typical symptoms of *C. perfringens* infection include, but are not limited to diarrhea, weight loss, appetite loss, bloating, flu-like symptoms, fever, abdominal pain, nausea, dehydration, colitis, or pseudomembraneous colitis.

In some embodiments, *C. perfringens* infection is treated with the bacterial strains of the present technology, or spores thereof, with subjects showing amelioration or elimination of one or more of the following symptoms: diarrhea, weight loss, appetite loss, bloating, flu-like symptoms, fever, abdominal pain, nausea, dehydration, colitis, or pseudomembraneous colitis.

In one aspect, the present technology provides a method for preventing or delaying the onset of *C. perfringens* infection or symptoms of *C. perfringens* infection in a subject at risk of having *C. perfringens* infection. In some embodiments, the bacterial strains of the present technology are formulated as a probiotic useful as a food supplement and for reestablishing beneficial bacteria in the intestinal tract. In some embodiments, the bacterial strains of the present technology are formulated as a live biotherapeutic product useful in pharmaceutical applications.

One aspect of the present technology includes methods of treating or preventing *L. monocytogenes* infection in a subject diagnosed as having, suspected as having, or at risk of having *L. monocytogenes* infection. In therapeutic applications, compositions or medicaments comprising a bacterial strain, or spore thereof, selected from the group consisting of ART24, ART4, and ART12, are administered to a subject suspected of, or already suffering from such a disease (such as, e.g., subjects exhibiting diarrhea, weight loss, appetite loss, bloating, flu-like symptoms, fever, abdominal pain, nausea, dehydration, colitis, or pseudomembraneous colitis), in an amount sufficient to cure, or at least partially arrest, the symptoms of the disease, including its complications and intermediate pathological phenotypes in development of the disease.

Subjects suffering from *L. monocytogenes* infection can be identified by any or a combination of diagnostic or prognostic assays known in the art. For example, typical symptoms of *L. monocytogenes* include, but are not limited to diarrhea, weight loss, appetite loss, bloating, flu-like symptoms, fever, abdominal pain, nausea, dehydration, colitis, or pseudomembraneous colitis.

In some embodiments, *L. monocytogenes* infection is treated with the bacterial strains of the present technology, or spores thereof, with subjects showing amelioration or elimination of one or more of the following symptoms: diarrhea, weight loss, appetite loss, bloating, flu-like symptoms, fever, abdominal pain, nausea, dehydration, colitis, or pseudomembraneous colitis.

In one aspect, the present technology provides a method for preventing or delaying the onset of *C. perfringens* infection or symptoms of *C. perfringens* infection in a subject at risk of having *C. perfringens* infection. In some embodiments, the bacterial strains of the present technology are formulated as a probiotic useful as a food supplement and for reestablishing beneficial bacteria in the intestinal tract. In some embodiments, the bacterial strains of the present technology are formulated as a live biotherapeutic product useful in pharmaceutical applications.

One aspect of the present technology includes methods of treating or preventing *V. parahaemolyticus* infection in a subject diagnosed as having, suspected as having, or at risk of having *V. parahaemolyticus* infection. In therapeutic applications, compositions or medicaments comprising a bacterial strain, or spore thereof, selected from the group consisting of ART24, ART4, and ART12, are administered to a subject suspected of, or already suffering from such a disease (such as, e.g., human subjects exhibiting gastroenteritis, diarrhea, abdominal cramps, nausea, vomiting, or wound infections; shrimp exhibiting Acute Hepatopancreatic Necrosis Disease (AHPND) or Early Mortality Syndrome (EMS); or salmon exhibiting hemorrhaging of the fins, eyes, and ventral surface), in an amount sufficient to cure, or at least partially arrest, the symptoms of the disease, including its complications and intermediate pathological phenotypes in development of the disease.

Subjects suffering from *V. parahaemolyticus* infection can be identified by any or a combination of diagnostic or prognostic assays known in the art. For example, typical symptoms of *V. parahaemolyticus* include, but are not limited to watery diarrhea, abdominal cramps, nausea, vomiting, or wound infections after coming into contact with contaminated seafood, such as contaminated shrimp or salmon.

In some embodiments, *V. parahaemolyticus* infection is treated with the bacterial strains of the present technology, or spores thereof, with subjects showing amelioration or elimination of one or more of the symptoms associated with *V. parahaemolyticus* infection.

VIII. Modes of Administration and Effective Dosages

Compositions of the present technology for use in preventing, ameliorating, or treating *C. difficile, C. perfringens, L. monocytogenes*, or *V. parahaemolyticus* infections and/or reducing the severity of one or more risk factors, signs, or symptoms associated with infection include live probiotic *B. amyloliquefaciens* bacteria according to the present technology, provided in the form of vegetative cells and/or spores. In some embodiments, the bacterial strain is lyophilized. The compositions of the present technology are administered to the subject in effective amounts (i.e., amounts that have desired therapeutic effect). The dose and dosage regimen will depend upon the degree of the infection in the subject, the characteristics of the particular *B. amyloliquefaciens* strain used, e.g., its therapeutic index, the subject, and the subject's history. The effective amount may be determined during pre-clinical trials and clinical trials by methods familiar to physicians and clinicians.

Compositions of the present technology may be formulated for adding to food, or used directly as a food supplement. The formulation may further include other probiotic agents or nutrients for promoting spore germination and/or bacterial growth.

Additional components of the compositions of the present technology may include a preservative selected from the group consisting of sucrose, sodium ascorbate, and glutathione. In some embodiments the preservative is a cryoprotectant selected from the group consisting of a nucleotide, a disaccharide, a polyol, and a polysaccharide. In some embodiments, the cryoprotectant is selected from the group consisting of inosine-5'-monophosphate (IMP), guanosine-5'-monophosphate (GMP), adenosine-5'-monophosphate (AMP), uranosine-5'-monophosphate (UMP), cytidine-5'-monophosphate (CMP), adenine, guanine, uracil, cytosine, guanosine, uridine, cytidine, hypoxanthine, xanthine, orotidine, thymidine, inosine, trehalose, maltose, lactose, sucrose, sorbitol, mannitol, dextrin, inulin, sodium ascorbate, glutathione, skim milk, and cryoprotectant 18.

The *B. amyloliquefaciens* bacterial strains described herein (i.e., ART24, ART4, and ART12) can be incorporated into pharmaceutical compositions for administration, singly or in combination, and given to a subject for the treatment or prevention of a disorder described herein. Such compositions typically include the active agent and a pharmaceutically acceptable carrier. As used herein the term "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions. Carriers can be solid-based dry materials for formulations in powdered form, and can be liquid or gel-based materials for formulations in liquid or gel forms, which forms depend, in part, upon the routes or modes of administration. In some embodiments, the pharmaceutically acceptable carrier comprises a polysaccharide, locust bean gum, an anionic polysaccharide, a starch, a protein, sodium ascorbate, glutathione, trehalose, sucrose, or pectin. In some embodiments, the polysaccharide comprises a plant, animal, algal, or microbial polysaccharide. In some embodiments, the polysaccharide comprises guar gum, inulin, amylose, chitosan, chondroitin sulphate, an alginate, or dextran. In some embodiments, the starch comprises rice starch.

Pharmaceutical compositions are typically formulated to be compatible with its intended route of administration. Examples of routes of administration include enteric (e.g., oral, sublingual, rectal) administration. A therapeutic composition can be formulated to be suitable for oral administration in a variety of ways, for example in a liquid, a powdered food supplement, a solid food, a packaged food, a wafer, tablets, troches, or capsules, e.g., gelatin capsules, and the like. In some embodiments, the therapeutic compositions of the present technology comprise lyophilized ART4, ART12, and/or ART24. In some embodiments, the lyophilized ART4, ART12, and/or ART24 is encapsulated. A therapeutic composition can be formulated to be suitable for rectal administration in a variety of ways, for example in a suppository, liquid enema, or foam. Other formulations will be readily apparent to one skilled in the art. pH can be adjusted with acids or bases, such as hydrochloric acid or sodium hydroxide.

For aquaculture applications, the pharmaceutical compositions of the present technology may be formulated as a fish feed or fish feed additive or as a bath (immersion) treatment agent.

Dosage, toxicity and therapeutic efficacy of any therapeutic agent can be determined by standard pharmaceutical procedures in cell cultures or experimental animals. The data obtained from the cell culture assays and animal studies can be used in formulating a range of dosage for use in humans. The dosage of such compounds may be within a range of circulating concentrations that include the ED50 with little or no toxicity. The dosage may vary within this range depending upon the dosage form employed and the route of administration utilized. For any compound used in the methods, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to determine useful doses in humans accurately.

In some embodiments, the compositions of the present technology contain in a one gram dosage formulation $10^8$ colony forming units (CFU) of viable *B. amyloliquefaciens* (i.e., ART24, ART4, and/or ART12) bacterium (i.e., vegetative cell) or bacterial spore. In some embodiments, the methods of the present technology involve the administration of about $10^4$ to about $10^{12}$ viable bacteria or spores per day. In some embodiments, the compositions of the present technology are delivered as lyophilized material or powder to be re-suspended for oral delivery or packaged into capsules. The lyophilized material and capsules may be coated for better enteric stability.

An exemplary treatment regimen entails administration once per day or once a week. In therapeutic applications, a relatively high dosage at relatively short intervals is sometimes required until progression of the disease is reduced or terminated, or until the subject shows partial or complete amelioration of symptoms of disease. Thereafter, the subject can be administered a prophylactic regime. In some embodiments, compositions of the present technology are administered to a subject once, twice, or three times per day for 10 to 14 days or until the subject is deemed cured of primary disease, not to be at risk for recurrence of primary disease, or not to be at risk for contracting the disease. In some embodiments, administration is paired with a shortened exposure to agents known in the art for the treatment of CDI, such as an antibiotic (including, but not limited to vancomycin, metronidazole or fidaxomicin), followed by once, twice, or three times daily dosing for 10 to 14 days or until the patient is deemed cured of primary disease or not to be at risk for recurrence of the disease. In some embodiments, methods of prophylaxis comprise administration of compositions of the present technology once, twice, or three times daily for 10 to 14 days or until the patient is deemed not to be at risk of contracting the disease in the case of patients known to be at risk for CDI (e.g. PPI use or immunosuppression).

The skilled artisan will appreciate that certain factors may influence the dosage and timing required to effectively treat a subject, including but not limited to, the severity of the disease or disorder, previous treatments, the general health and/or age of the subject, and other diseases present. Moreover, treatment of a subject with a therapeutically effective amount of the therapeutic compositions described herein can include a single treatment or a series of treatments.

IX. Combination Therapy with *B. amyloliquefaciens* Strains of the Present Technology In some embodiments, the *B. amyloliquefaciens* strains of the present technology, or spores thereof, may be combined with one or more additional therapies for the prevention or treatment of CDI. Additional therapeutic agents include, but are not limited to, one or more additional therapeutic agents selected from the group consisting of: metronidazole, fidaxomicin, vancomycin, nitazoxanide, fecal microbiota transplant, and anti-toxin B monoclonal antibody.

In some embodiment, an additional therapeutic agent is administered to a subject in combination with the *B. amyloliquefaciens* strains of the present technology, or spores thereof, such that a synergistic therapeutic effect is produced. For example, administration of ART24, ART4, and/or ART12 with one or more additional therapeutic agents for the prevention or treatment of CDI will have greater than additive effects in the prevention or treatment of the disease.

In any case, the multiple therapeutic agents may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. In addition, the combination methods, compositions and formulations are not to be limited to the use of only two agents.

EXAMPLES

The following examples are provided by way of illustration only and not by way of limitation. Those of skill in the art will readily recognize a variety of non-critical parameters that could be changed or modified to yield essentially the same or similar results. The examples should in no way be construed as limiting the scope of the present technology, as defined by the appended claims. For each of the examples below, any bacterial strain described herein could be used. By way of example, the bacterial strain used in the examples below could be ART24, ART4, ART12, or combinations thereof.

Materials and Methods

Human stool samples. Stool samples were collected from male and female subjects (N=22) in the following age ranges: 20-39 years (N=14); 40-59 years (N=3); 60-79 years (N=4); and 80-99 years (N=1). Stool samples were received in the laboratory and processed fresh within 8-12 h after faeces were voided. On the day of analysis, a slurry was prepared using maximum recovery diluent (MRD) (CM0733, Oxoid). These slurries were mixed with equal volumes of ethanol for two hours after which the samples were serially diluted in MRD and spread plated on to the surface of Brain Heart Infusion (BHI) (1.10493.0500, Merck) agar plates. These plates were then incubated aerobically for 24 h.

Identification of anti-*Clostridium difficile* strains (Well Diffusion Assay (WDA)). Bacterial strains were isolated from the samples and analyzed for anti-*Clostridium difficile* activity. The BHI agar plates with the serially diluted bacterial colonies from the stool samples were then overlaid with Reinforced *Clostridium* Media (RCM) (1.015410.0500 Merck) sloppy agar that had been inoculated with *C. difficile*. Potential anti-*C. difficile* colonies were identified by the presence of a zone of inhibition surrounding a bacterial colony. *C. difficile* was inoculated at 1% (v/v) into RCM agar and the plates were allowed to harden. Wells were made in the hardened agar plates using sterile Pasteur pipettes. Potential anti-*C. difficile* bacterial strains were isolated from the overlay plate and re-streaked to ensure a pure colony. Potential anti-*C. difficile* bacterial strains were grown in BHI broth aerobically, shaking at 200 rpm and incubated at 37° C. Overnight cultures of the bacterial strains were centrifuged and the supernatants pH neutralized and filter sterilized with 0.22 µm filters to ensure cell free supernatants (CFS). Fifty microlitres of the bacterial CFS were dispensed into the wells of the RCM plate anaerobically and the plate was allowed to incubate for 24 h. Anti-*C. difficile* activity was assessed by examining the presence or absence of zones of inhibition surrounding the wells. Colonies showing antimicrobial activity against the overlaid *C. difficile* strain were purified and stocked at −80° and designated as ART24, ART4, and ART12 (also designated herein as "ART024(2)," "ART04-A4," and "ART012-Aer1," respectively).

Isolated strains were aerobically grown at 37° C. for 24 hrs, shaking at 200 rpm, on Brain Heart Infusion (BHI) broth and/or static on agar.

Genotypic characterization and identification of species level using universal 16S rRNA primers. Based on the results of the 16S rRNA gene sequencing, ART24, ART4, and ART12 were each identified as members of the *B. amyloliquefaciens* species. Using the DNA sequence of the DNA gyrase subunit A (gyrA) identified from the whole genome sequences of each strain, ART24, ART4, and ART12 were further identified as *B. velezensis/B. amyloliquefaciens* subsp. *plantarum* and members of the operational group *Bacillus amyloliquefaciens*.

Glycerol (G5516, Sigma) stocks of the strains were stored at −80° C. (800 µL of culture grown in BHI broth added to 200 µL 100% glycerol).

Figure 1B:
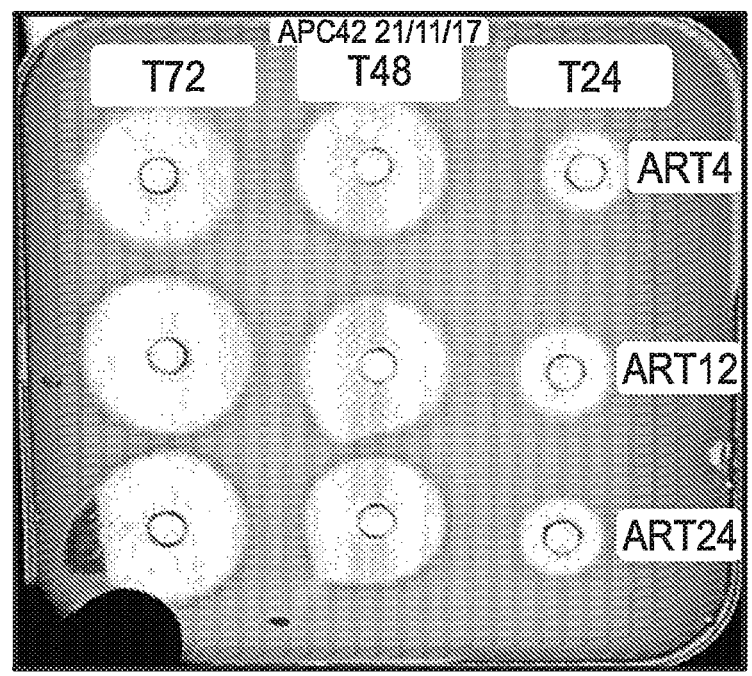

Example 1: *Bacillus amyloliquefaciens* Strains Exhibit Anti-*C. difficile* Activity This example demonstrates that *B. amyloliquefaciens* strains of the present technology exhibit potent anti-*C. difficile* activity (FIGS. 1A and 1B).

Bacterial strains. Using the well diffusion assay (WDA) method described above, the prepared supernatants of each of the three candidates, ART24, ART4, ART12, were tested against a clinical isolate of *C. difficile*. FIGS. 1A and 1B show the large zones of activity achieved against this strain.

Accordingly, these results show that the *B. amyloliquefaciens* strains of the present technology are useful in methods of inhibiting *C. difficile* growth.

Example 2: Anti-*C. difficile* Activity of the *B. amyloliquefaciens* Strains of the Present Technology are Insensitive to Digestive Proteases This example demonstrates that the *B. amyloliquefaciens* strains of the present technology are insensitive to digestive proteases such as trypsin, pepsin, chymotrypsin, and proteinase-K.

Figure 2A:
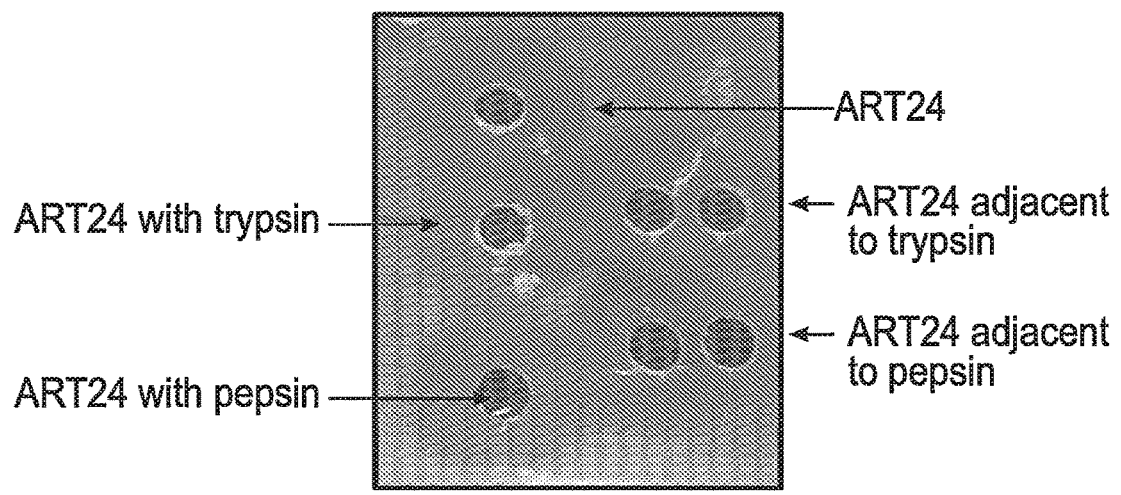

To test the (in)sensitivity of ART24 supernatant to pepsin and trypsin, WDA were carried out against *C. difficile* whereby preparations of each protease were individually added directly to the supernatant or adjacent to the supernatant and incubated for 24 hours at 37° C. anaerobically. As shown in FIG. 2A, there was no decrease in zone size in comparison to the untreated control and therefore, as a whole, the anti-*C. difficile* bioactivity exhibited by supernatant from ART24 culture is insensitive to the proteases.

Figure 2B:
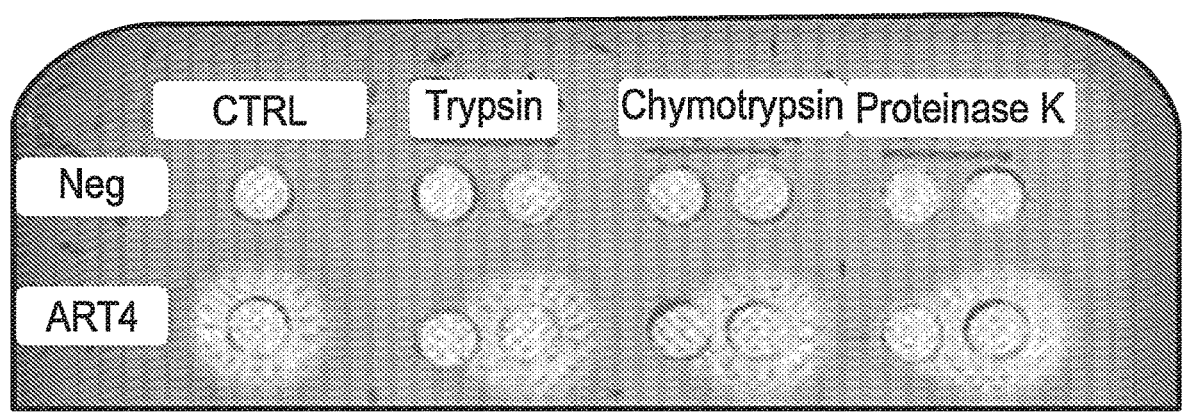

To test the (in)sensitivity of ART4 supernatant to trypsin, chymotrypsin, and proteinase-K, WDA were carried out against *C. difficile* whereby preparations of each protease were individually added adjacent to the supernatant and incubated for 24 hours at 37° C. anaerobically. As shown in FIG. 2B, there was no decrease in zone size in comparison to the untreated control and therefore, as a whole, the anti-*C. difficile* bioactivity exhibited by supernatant from ART4 culture is insensitive to the proteases.

As shown in FIGS. 2A and 2B, none of the digestive enzymes tested had an inhibitory effect on supernatants from ART24 or ART4. Accordingly, these results show that pharmaceutical compositions comprising the bacterial strains of the present technology will retain their anti-*C. difficile* activity after oral administration.

Example 3: *B. amyloliquefaciens* Strains of the Present Technology Contain Masses for Amylocyclicin This example demonstrates that the *B. amyloliquefaciens* strains of the present technology produce amylocyclicin, a bacteriocin having effects against Gram-positive bacteria, such as *C. difficile*.

Figure 3A:
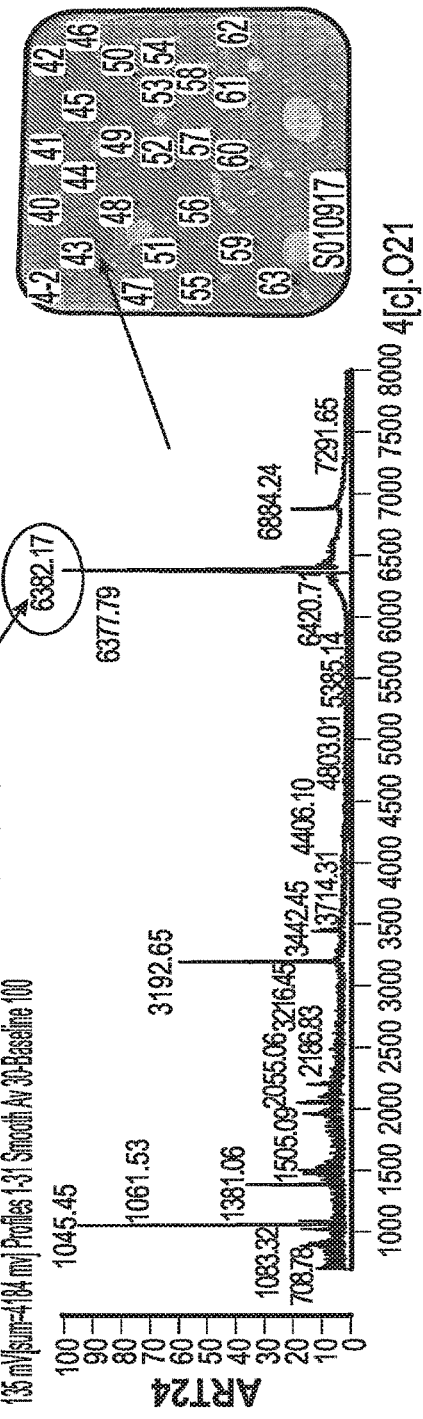
Figure 3B:
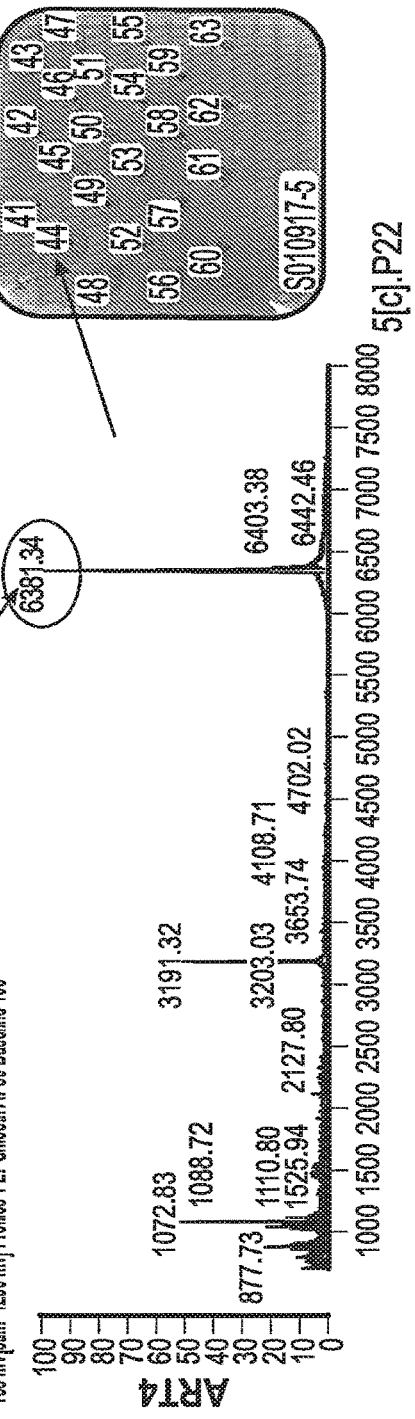
Figure 3C:
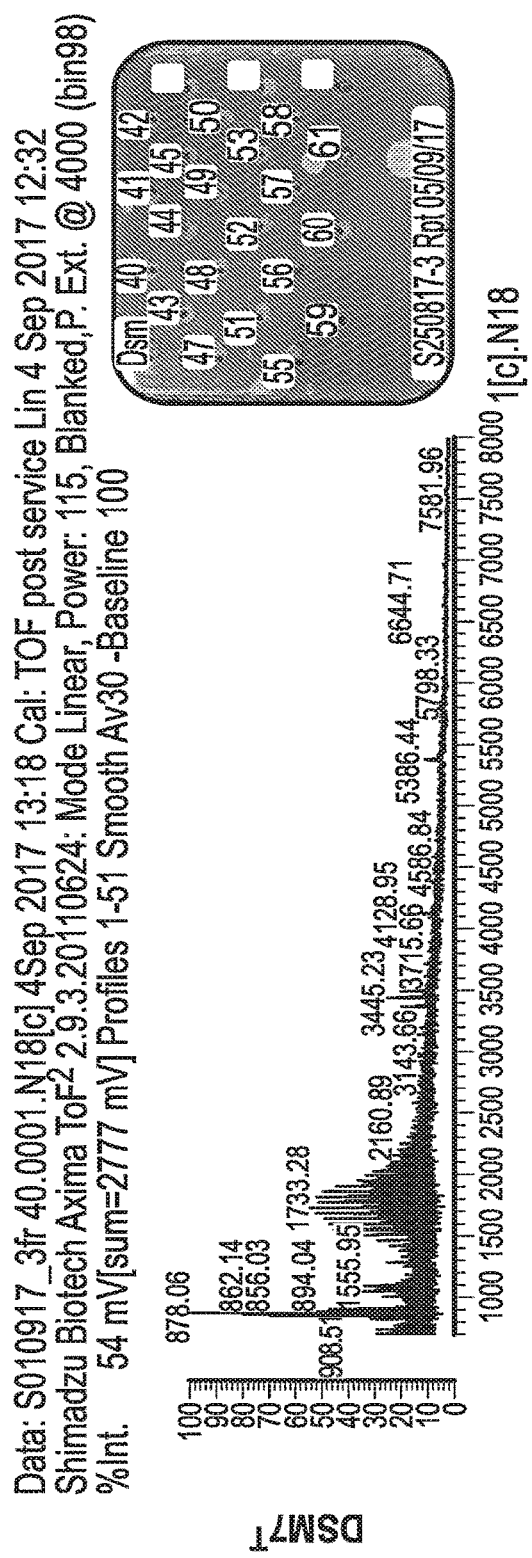
Figure 3D:
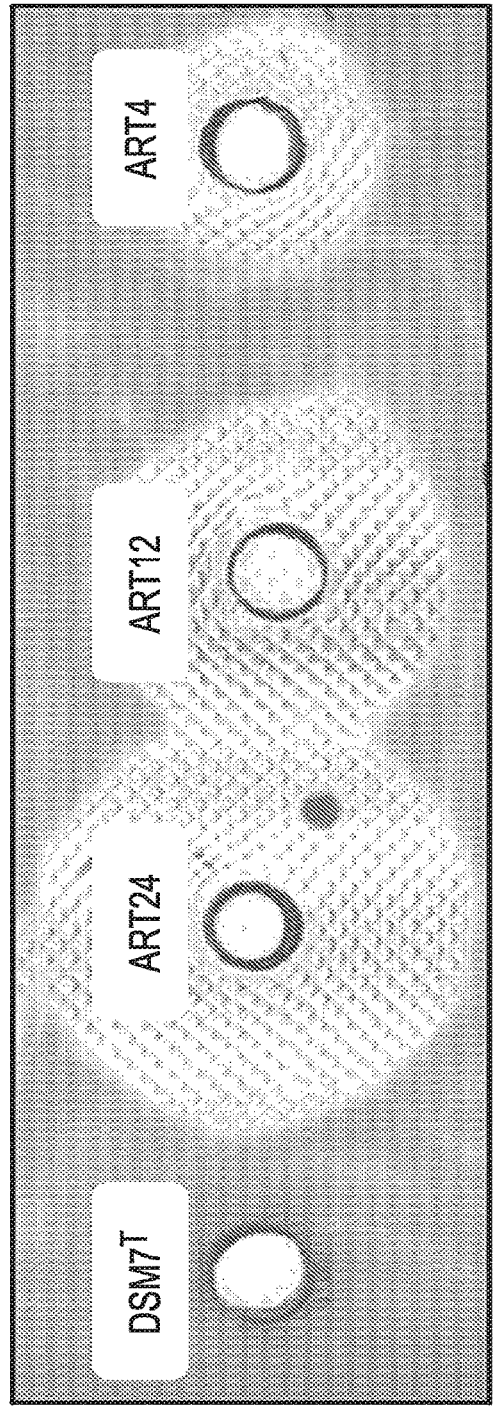

As shown in FIGS. 3A and 3B, mass spectrometry (MS) analysis of the culture supernatants of ART24 and ART4 revealed the presence of amylocyclicin at m/z 6,382.17 and 6,381.34, respectively. However, the bacteriocin was completely absent in the DSM7$^T$ strain (FIG. 3C).

Briefly, 150 mL of culture supernatant was centrifuged and the cells were mixed with 70% propan-2-ol 0.1% TFA (IPA) and supernatant was applied to a column containing 30 g of XAD, washed with 250 mL 30% ethanol and antimicrobial activity eluted with IPA. Cell and SN XAD samples were passed through a 5 g, 20 mL C18 SPE column pre-equilibrated with methanol and water. The column was washed with 15% ethanol and antimicrobial activity eluted in 70% 2-propan-2-ol 0.1% TFA. The IPA eluents were concentrated and 1 mL (of 3 mL) applied to a semi prep C12 Proteo Jupiter (10×250 mm, 4µ, 90 Å) RP-HPLC column running a 27.5-85% acetonitrile 0.1% TFA gradient where buffer B is 90% acetonitrile 0.1% TFA. Eluent was monitored at 214 nm and fractions were collected at 1 minute intervals. MALDI TOF mass spectrometry was used to assess the size of the peptides.

The fractions generated during the HPLC run were then tested in WDA against *C. difficile* to identify the region of anti-*C. difficile* activity. Active fractions visible in the WDA were then analyzed on the MALDI-TOF mass spectrometer to identify the active component. The mass spectra for the supernatants of ART24 and ART4 indicate that amylocyclicin and plipastatin are potential anti-*C. difficile* components of the supernatants (FIGS. 3A; 3B; 9C; 9E).

Accordingly, these results show that the *B. amyloliquefaciens* strains of the present technology produce amylocyclicin having anti-*C. difficile* effects as shown by the well diffusion assays (WDA) of FIGS. 3A and 3B.

Example 4: The anti-*C. difficile* activity of the *B. amyloliquefaciens* Strains of the Present Technology are Insensitive to Proteinase-K This example demonstrates that the cell free supernatants of *B. amyloliquefaciens* strains of the present technology are insensitive to proteinase-K (ProK), which degrades amylocyclicin.

Figure 4A:
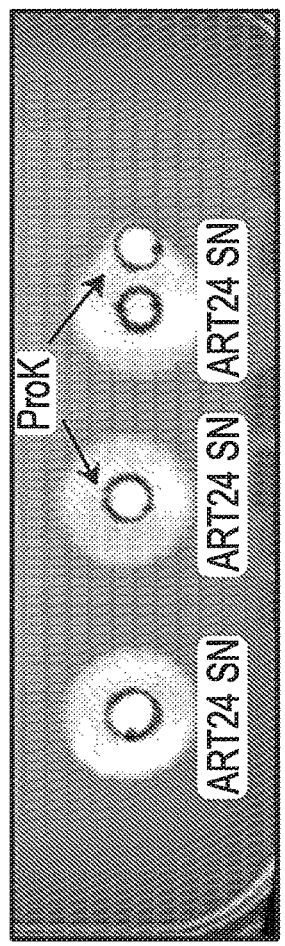

As shown in FIG. 4A, supernatant collected from ART24 cultures is active in the presence of ProK, indicating that amylocyclicin is not the sole anti-*C. difficile* microbial produced by the strain.

Figure 4B:
Figure 4B:
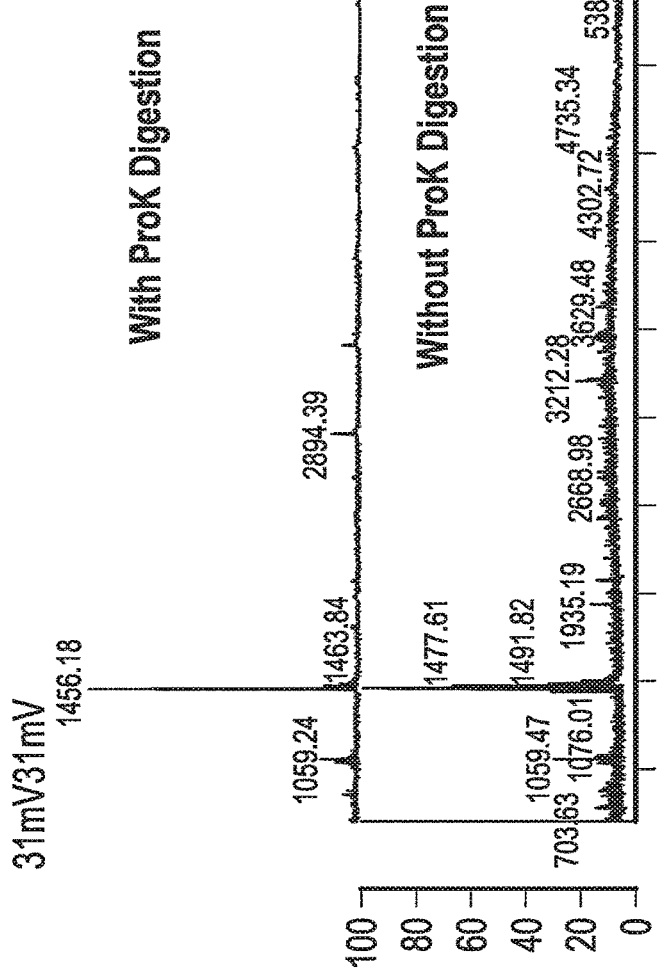

Briefly, a WDA was carried out using *C. difficile* as the indicator whereby proteinase-K was added directly or added to an adjacent well without any decrease or inhibition of zone size in either when compared to an untreated control. Mass spectrometric analysis shows that anti-*C. difficile* activity is maintained when the amylocyclicin peak is lost in the presence of proteinase-K (FIG. 4B).

As shown in Table 1, based on searches performed in the anti-SMASH (antibiotics & Secondary Metabolite Analysis Shell) database, the genome sequences of the *B. amyloliquefaciens* strains of the present technology (ART4, ART12 and ART24) predict overlapping, but non-identical, antimicrobial profiles relative to the anti-*C. difficile* negative strain DSM7$^T$.

GenBank files of the whole genome sequences of ART4, ART12 and ART24 were uploaded into anti-SMASH database with the default features selected and the antimicrobial regions in the *Bacillus* genomes were then compared to known anti-microbial clusters.

48 hours anaerobically at 37° C. A 4.1 log reduction was seen when comparing the count from *C. difficile* inoculated singly at 24 hours and that achieved when co-cultured with *B. amyloliquefaciens* ART24 for 24 hours. If expressed as the reduction in *C. difficile* numbers at T0, the co-culture with *B. amyloliquefaciens* ART24 is just less than a 2 log reduction.

Figure 5A:
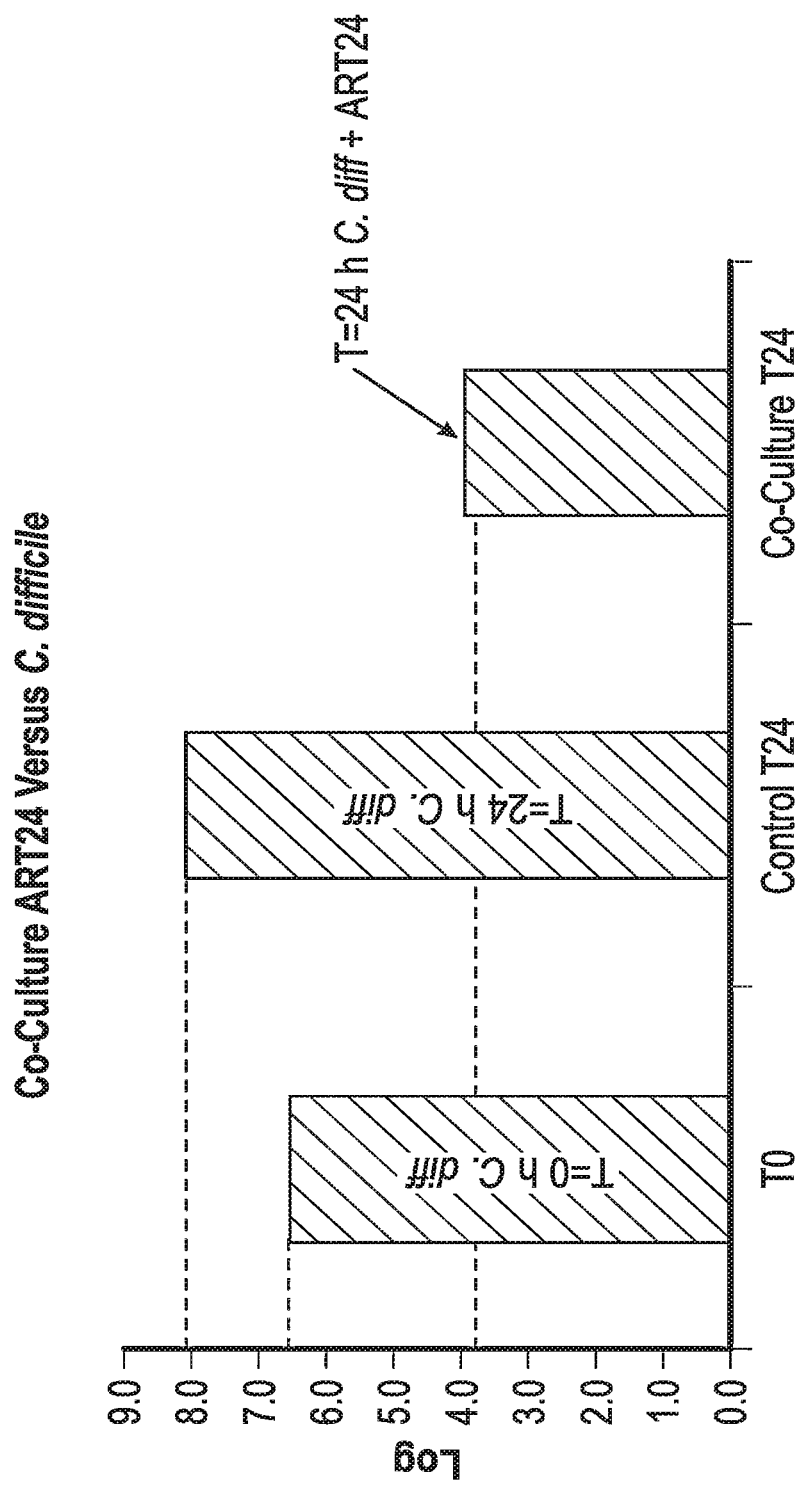
Figure 5B:
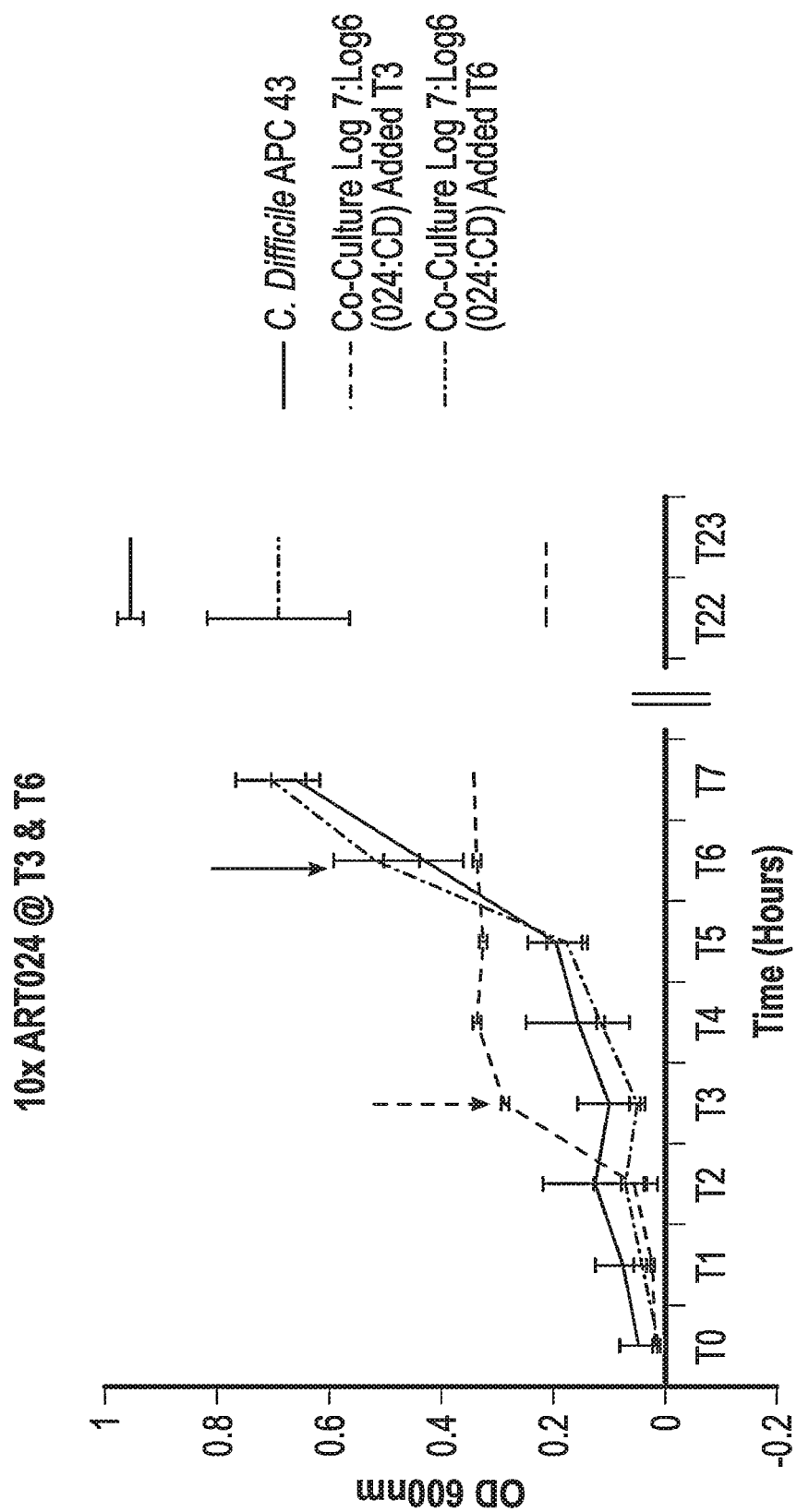

As shown in FIG. 5B, inoculation of 10× ART24 into an ongoing *C. difficile*, culture at T3h and T6h, for 24 hours results in a decrease in *C. difficile* growth per OD reading.

Bacterial strains. Using the anaerobic co-culture method described above, the addition of 10:1 ratio of ART024 into a *C. difficile* culture entering log phase (T3h post initial *C. difficile* inoculation) results in *C. difficile* growth inhibition compared to unexposed control culture.

Bacterial strains. Using the anaerobic co-culture method described above, the addition of 10:1 ratio of ART024 into a *C. difficile* culture into log phase (T6h post *C. difficile* inoculation) results in *C. difficile* growth inhibition compared to unexposed control culture.

Accordingly, these results show that compositions comprising the *B. amyloliquefaciens* strains of the present tech-

TABLE 1 anti-SMASH antimicrobial operon summary.

| Type | Most similar to known cluster | Strains and percentage identity to known cluster/mature peptide | | | |
|---|---|---|---|---|---|
| | | ART4 | ART12 | ART24 | DSM7 |
| Lantipeptide | Locillomycin | — | — | 35% | — |
| Thiopeptide | Thiopeptide | — | No percentage given | — | — |
| Bacteriocin | Amylolysin | — | 100% | — | — |
| NRPS | Surfactin | 82% | 82% | 86% | 82% |
| PKS | Macrolactin | 100% | 100% | 100% | — |
| PKS/NRPS | Bacillaene | 100% | 100% | 100% | 100% |
| PKS/NRPS | Fengycin | 100% | 100% | 100% | 93% |
| PKS | Difficidin | 100% | 100% | 100% | — |
| Bacteriocin-NRPS | Bacillibactin | 100% | 100% | 100% | 100% |
| Other | Bacilysin | 100% | 100% | 100% | 85% |
| Bacteriocin | Mersacidin | 100% | — | — | — |
| PKS | Mycosubtilin/Gramacidin? | No percentage given | — | — | — |
| Bacteriocin | Amylocyclicin | 100% | 100% | 100% | — |

— = Not present in the genome annotation

Accordingly, these results show that the *B. amyloliquefaciens* strains of the present technology possess a diverse range of antimicrobial activities.

Example 5: The *B. amyloliquefaciens* Strains of the Present Technology are Cidal to *C. difficile* in Liquid Co-Culture Assay As shown in FIG. 5A, co-culturing ART24 and *C. difficile*, inoculated at equal levels, for 24 hours results in a 4.1 log reduction in *C. difficile* counts.

Briefly, 1004, aliquots of 18 hour cultures of *B. amyloliquefaciens* ART24 and *C. difficile* were co-inoculated and inoculated separately into preconditioned 10 mL of BHI broth and incubated anaerobically at 37° C. for 24 hours. *C. difficile* enumeration was achieved by plating onto Brazier's CCEY agar (LAB160, Lab M) and allowed to incubate for nology are useful in methods of treating or preventing *C. difficile* infection or *Clostridium difficile*-associated disease (CDAD).

Figure 6A:
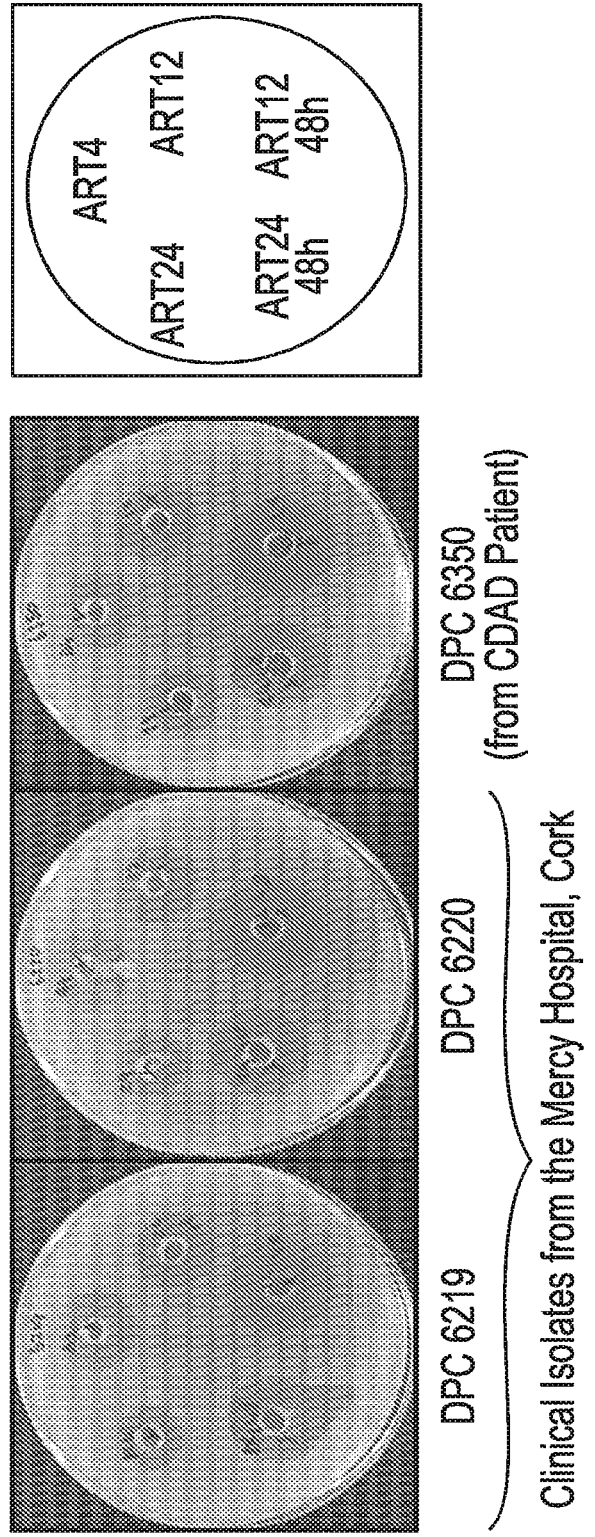
Figure 6B:
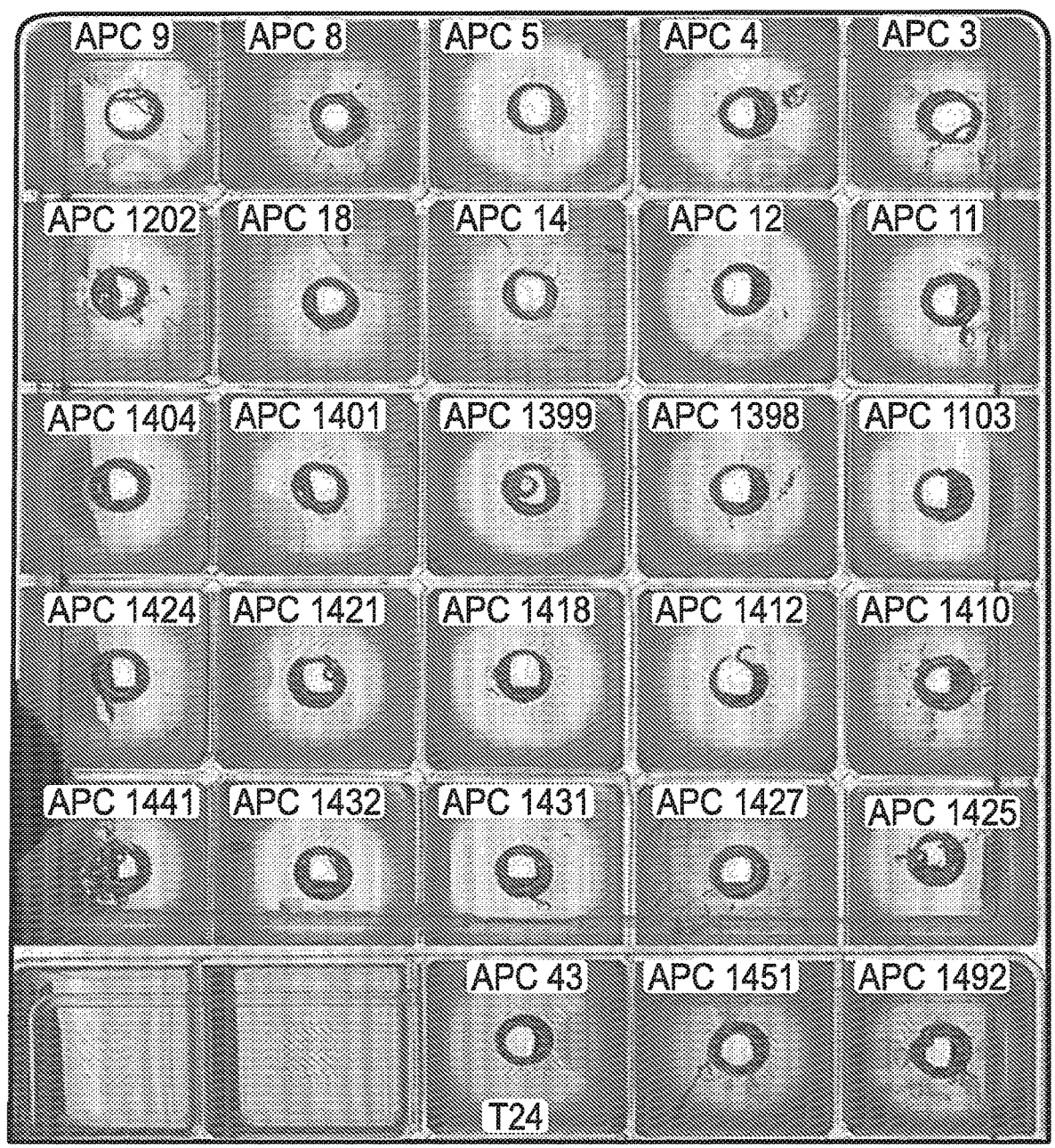

Example 6: The *B. amyloliquefaciens* Strains of the Present Technology Demonstrate Activity Against *C. difficile* Clinical Isolates As shown in FIGS. 6A and 6B, supernatants of ART4, ART12, and ART24 demonstrate anti-*C. difficile* activity against a panel of several different clinical *C. difficile* isolates with a range of ribotypes (DPC 6219, DPC 6220, and DPC 6350 (FIG. 6A), and ART24 against 28 other contemporary clinical isolates (FIG. 6B; Table 2)). ART4, ART12, and ART24 also demonstrated activity against *C. difficile* isolates EM304 and APC43 (data not shown).

TABLE 2

*Clostridium difficile* panel

| APC No. | Genus | Species | Isolated from | Ribotype | Other designation |
|---|---|---|---|---|---|
| 3 | Clostridium | difficile | Ulcerative colitis patient | R003 | |
| 4 | Clostridium | difficile | Ulcerative colitis patient | R010 | |
| 5 | Clostridium | difficile | Ulcerative colitis patient | R020 | |
| 8 | Clostridium | difficile | Ulcerative colitis patient | R062 | |
| 9 | Clostridium | difficile | Ulcerative colitis patient | R050 | |
| 11 | Clostridium | difficile | Healthy adult | R026 | |
| 12 | Clostridium | difficile | Ulcerative colitis patient | R131 | |
| 17 | Clostridium | difficile | CDI patient | R001 | |
| 18 | Clostridium | difficile | CDI patient | R106 | |
| 43 | Clostridium | difficile | Abdominal wound | R078 | VPI 10463, ATCC 43255 |
| 1202 | Clostridium | difficile | Human isolate | R017 | M68 |
| 1203 | Clostridium | difficile | Human isolate | R012 | 630 |
| 1398 | Clostridium | difficile | CF patient | R014 | |
| 1399 | Clostridium | difficile | CF patient | R002 | |
| 1401 | Clostridium | difficile | CF patient | R126 | |
| 1404 | Clostridium | difficile | CF patient | R140 | |
| 1410 | Clostridium | difficile | CF patient | R015 | |
| 1412 | Clostridium | difficile | CF patient | R046 | |
| 1418 | Clostridium | difficile | CF patient | R039 | |
| 1421 | Clostridium | difficile | CF patient | R078 | |
| 1424 | Clostridium | difficile | CF patient | R011 | |
| 1425 | Clostridium | difficile | CF patient | R005 | |
| 1427 | Clostridium | difficile | CF patient | R092 | |
| 1431 | Clostridium | difficile | CF patient | R087 | |
| 1432 | Clostridium | difficile | CF patient | R356 | |
| 1441 | Clostridium | difficile | Thuricin-CD resistant mutants of *C. difficile* | R001 | Liv024 R001 mutant 9 |
| 1442 | Clostridium | difficile | Thuricin-CD resistant mutants of *C. difficile* | R015 | TL174 R015 mutant 1 |
| 1451 | Clostridium | difficile | Thuricin-CD resistant mutants of *C. difficile* | R027 | CD196 R027 mutant 1 |

Briefly, well diffusion assays (WDA) were used to examine the effect of the *Bacillus amyloliquefaciens* supernatants (from the strains and from different timepoints) against clinical *C. difficile* isolates. Fifty microlitres of supernatant was added to wells in RCM agar inoculated (1% v/v) with each clinical isolate.

These results demonstrate that compositions comprising the *B. amyloliquefaciens* strains of the present technology are useful in methods of treating or preventing *C. difficile* infection or *Clostridium difficile*-associated disease (CDAD).

Example 7: The *B. amyloliquefaciens* Strains of the Present Technology are Selective for *C. difficile* and *B. thuringiensis*

To identify a spectrum of activity for the supernatants, a panel of commensal organisms (*Lactobacillus reuteri*, *Lactobacillus rhamnosus*, *Staphylococcus capitis*), and *Bacillus thuringiensis* were compared to *C. difficile*. Well diffusion assays (WDA) were used to compare the supernatants from the 3 strains and from 24 h, 48 h cultures of each. The *lactobacillus* strains were inoculated into de Mann Rogosa Sharpe (MRS) (288130, Difco) agar; *S. capitis* and *B. thuringiensis* were inoculated into BHI agar, and *C. difficile* was inoculated into RCM agar, all strains were inoculated at 1% (v/v). No zones of inhibition were identified against Lb. reuteri, Lb. rhamnosus, and *S. capitis*. Zones of inhibition were identified for all strains and culture timepoints against *B. thuringiensis* and *C. difficile*.

Figure 7A:
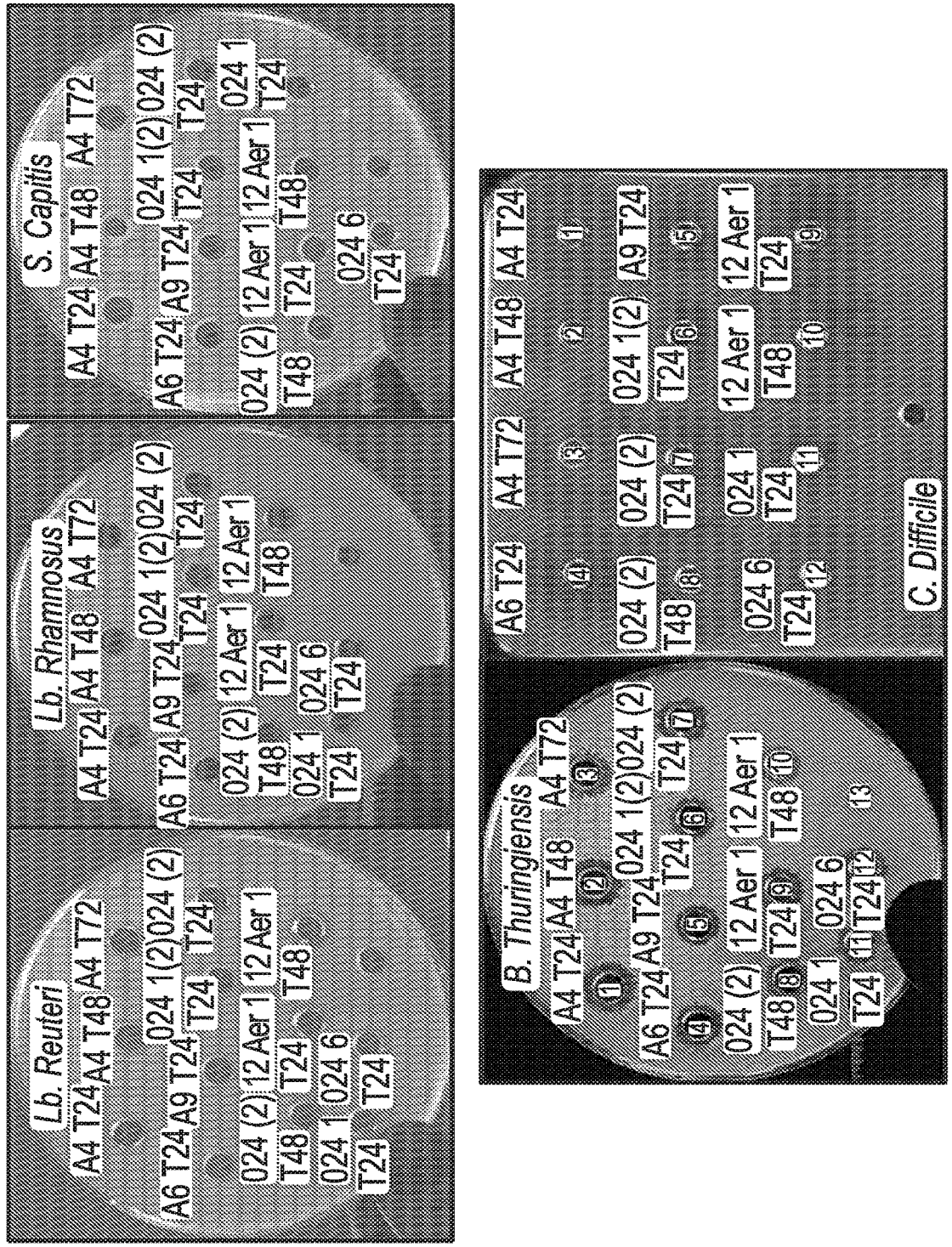

As shown in FIG. 7A, supernatants from the ART4 ("A4"), ART12 ("12 Aer 1"), and ART24 ("024(2)") strains are selectively active against *C. difficile* and *B. thuringiensis*, and not against the human commensals tested.

Figure 7B:
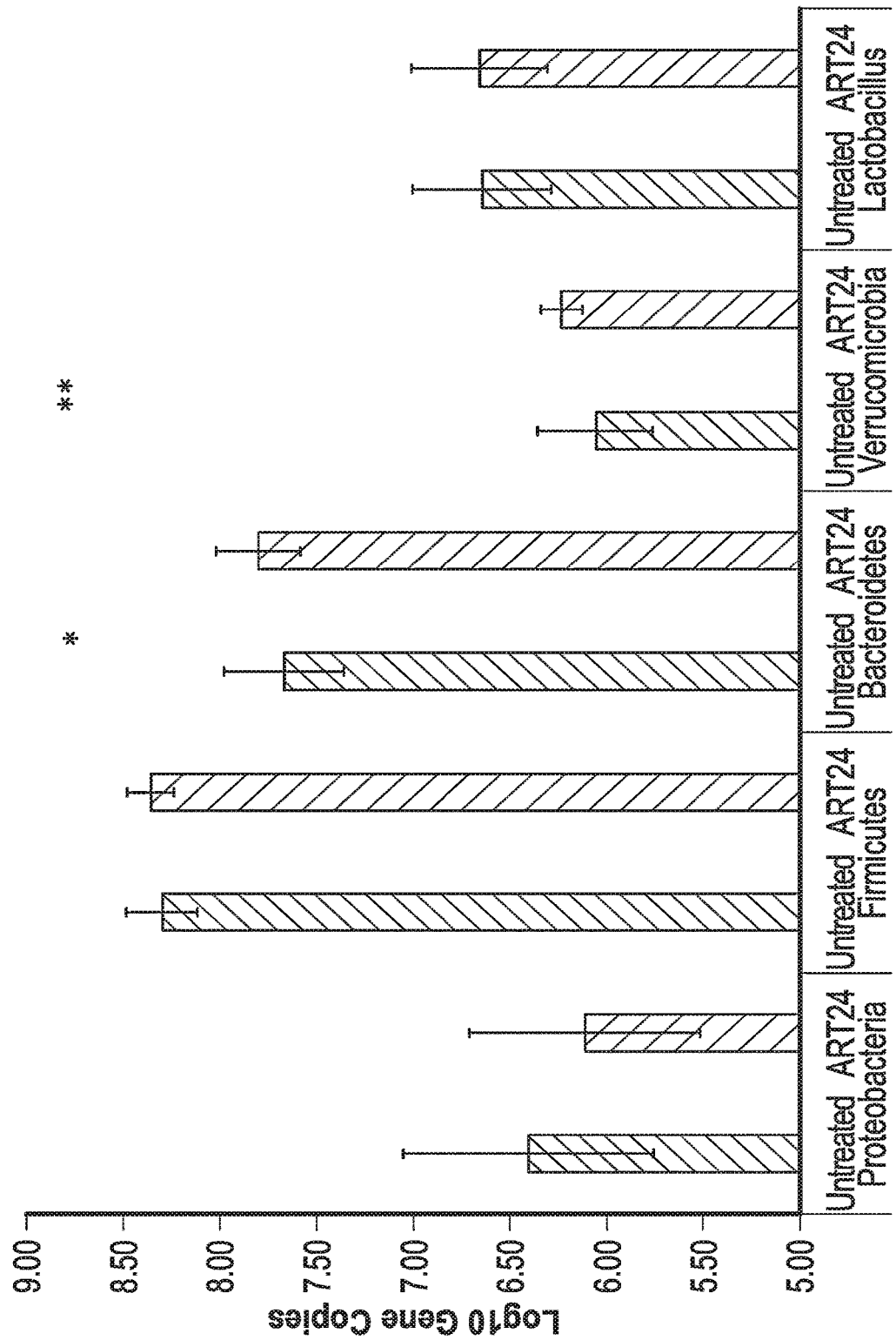

As shown in FIG. 7B, fresh ART24 ("024(2)") strains added to in vitro human colonic microbiota samples are sparing the main human colonic phyla investigated, namely proteobacteria, firmicutes, Bacteroidetes, verrucomicrobia, and *lactobacillus*

These results demonstrate that the compositions comprising the *B. amyloliquefaciens* strains of the present technology are useful in methods for selectively treating or preventing *C. difficile* infection or CDAD, without depleting commensal bacterial populations.

Example 8: The *B. amyloliquefaciens* Strains of the Present Technology are within EFSA Antibiotic Susceptibility Guidelines and Do Not Contain Virulence Factors or Pathogenicity Islands As demonstrated by Table 3, the *B. amyloliquefaciens* strains of the present technology (e.g., ART4, ART12 and ART24 strains) are within the European Food Safety Authority (EFSA) guidelines. The minimum inhibitory concentration (MIC) of the listed antimicrobials is expressed as µg/mL. Additional studies following EFSA testing recommendations were performed on lyophilized ART24 lots CO-33-10A2 and CO-33-12A2 and Research and Master Cell Banks CO-33-ART24 BHI and CO-33-ART24 SYD, and those results are shown in Table 4.

TABLE 3

B. amyloliquefaciens strains are within EFSA antibiotic susceptibility guidelines

| | B. amyloliquefaciens MIC (μg/mL) | | | EFSA guidelines |
|---|---|---|---|---|
| | ART4 | ART12 | ART24 | |
| Ampicillin | 0.12 | 0.25 | 0.25 | n.r. |
| Vancomycin | 0.5 | 0.5 | 0.5-1 | 4 |
| Gentamicin* | ≤0.5 | ≤0.5 | ≤0.5 | 4 |
| Kanamycin* | ≤2 | ≤2 | ≤2 | 8 |
| Streptomycin | 4 | 4 | 4 | 8 |
| Erythromycin | 0.12 | 0.12 | 0.12 | 4 |
| Clindamycin | 0.5 | 1 | 0.5-1 | 4 |
| Tetracycline | 1 | 8 | 4 | 8 |
| Chloramphenicol | 2 | 4 | 4 | 8 |
| Neomycin* | ≤0.5 | ≤0.5 | ≤0.5 | — |
| Penicillin | 0.12 | 0.5 | 0.12-0.5 | — |
| Quinupristin-dalfopristin | 4 | 4 | 4 | — |
| Linezolid | 0.5 | 0.5 | 0.5 | — |
| Trimethoprim | ≤0.12 | ≤0.12 | <≤0.12 | — |
| Ciprofloxacin* | ≤0.25 | ≤0.25 | <≤0.25 | — |
| Rifampicin | 0.25 | 0.5 | 0.5 | — |

Average results from N = 6.
*No growth with the lowest concentration in the plate.

antibiotic to inhibit visible growth. The prefabricated panels VetMIC Lact-1 & Lact-2 (SVA, Uppsala, Sweden) comprising the antibiotics ampicillin, vancomycin, gentamicin, kanamycin, streptomycin, erythromycin, clindamycin, tetracycline, chloramphenicol, neomycin, penicillin, quinupristin-dalfopristin, linezolid, trimethoprim, ciprofloxacin and rifampicin were used.

The absence of antibiotic resistance in the strains of the present technology precludes the risk of horizontal transfer of antibiotic resistance.

Moreover, searches conducted with KEGG, RAST SEED Viewer, IslandViewer 4 and ACT comparisons to known Bacillus species that produce toxins, etc., did not reveal any virulence factors or pathogenicity islands in the genomes of the B. amyloliquefaciens strains of the present technology. Accordingly, these results demonstrate the probiotic safety of the strains in that they lack the propensity to confer resistance to commensals and/or pathogens.

Example 9: Co-Administration of B. amyloliquefaciens Strains of the Present Technology and Other Agents for the Treatment of Clostridium difficile-Associated Disease (CDAD)

This example demonstrates that, as shown in Table 5, the B. amyloliquefaciens strains of the present technology are resistant to high levels of metronidazole (Met), but are fully sensitive to fidaxomicin (FDX).

TABLE 4

B. amyloliquefaciens strains (ART24) are within EFSA antibiotic susceptibility guidelines

| | MIC in mg/L (interpretation) for ART24 for all 4 sources[a] | | | |
|---|---|---|---|---|
| Antimicrobial | CO-33 ART 24 BHI | CO-33 ART 024 SYD | CO-33-10A2 | CO-33-12A2 |
| Ampicillin | ≤0.03 (S) | ≤0.03 (S) | ≤0.03 (S) | ≤0.03 (S) |
| Chloramphenicol | 2 (S) | 2 (S) | 2 (S) | 2 (S) (S) |
| Ciprofloxacin | ≤0.03 (S) | ≤0.03 (S) | ≤0.03 (S) | ≤0.03 (S) |
| Clindamycin | 0.25 (S) | 0.25 (S) | 0.12 (S) | 0.25 (S) |
| Erythromycin | 0.12 (S) | 0.12 (S) | 0.06 (S) | 0.06 (S) |
| Fidaxomicin | 4 | 4 | 2 | 4 |
| Gentamicin | ≤0.06 (S) | ≤0.06 (S) | ≤0.06 (S) | ≤0.06 (S) |
| Kanamycin | ≤0.5 (S) | ≤0.5 (S) | ≤0.5 (S) | ≤0.5 (S) |
| Linezolid | 0.5 | 0.5 | 0.25 | 0.5 |
| Metronidazole (aerobic) | >64 | >64 | >64 | >64 |
| Metronidazole (anaerobic) | 64 | 64 | 64 | 64 |
| Neomycin | ≤0.12 | ≤0.12 | ≤0.12 | ≤0.12 |
| Penicillin | ≤0.03 (S) | 0.06 (S) | ≤0.03 (S) | ≤0.03 (S) |
| Quinupristin-dalfopristin | 2 | 2 | 1 | 2 |
| Rifampicin | 0.25 (S) | 0.25 (S) | 0.25 (S) | 0.25 (S) |
| Streptomycin | 1 (S) | 2 (S) | 1 (S) | 1 (S) |
| Tetracycline | 2 (S) | 2 (S) | 2 (S) | 2 (S) |
| Trimethoprim | <0.25 | <0.25 | <0.25 | <0.25 |
| Vancomycin | 0.5 (S) | <0.25 (S) | <0.25 (S) | <0.25 (S) |

[a]Categorical interpretations using CLSI M45 (2015) breakpoint criteria, as available. MIC interpretations for kanamycin and streptomycin used European Food Safety Authority cutoff values (2012).

Briefly, material from 3-5 colonies of Bacillus amyloliquefaciens were selected and suspended in 4 mL of MRD to obtain a cell concentration of ~1×10$^8$ CFU/mL. From this suspension 464, was transferred in to 23 mL of 90% Iso-Sensitest Broth (CM0473, Oxoid) containing 10% BHI broth to end with a final inoculum concentration of 5×10$^5$ CFU/mL. The wells of the prefabricated 96-well plates were filled with 100 μL of the final suspension. The plates were sealed with an AeraSeal (A9224, Sigma Aldrich) sealing film (to facilitate growth of the aerobic Bacillus strains. The plates were then incubated for 24 hr at 37° C. The results are recorded after 24 hours as the lowest concentration of the

TABLE 5

B. amyloliquefaciens strain susceptibility to metronidazole (Met) and fidaxomicin (FDX)

| | FDX (μg/ml) | Met (μg/ml) |
|---|---|---|
| ART4 | <1 | 128 |
| ART12 | <1 | 64 |
| ART24 | 2 | 128 |

CLSI standard method; all triplicates. MIC of FDX against clinically isolated C. difficile (0.004-8 μg/mL). MIC of Met against clinically isolated C. difficile (0.02-4 μg/mL).

CLSI standard method; all triplicates. MIC of FDX against clinically isolated *C. difficile* (0.004-8 µg/mL). MIC of Met against clinically isolated *C. difficile* (0.02-4 µg/mL).

Briefly, minimum inhibitory concentration assays were carried out in triplicate using 96-well plates (Sarstedt). Two-fold serial dilutions from an initial concentration of 512 ng/mL of each antibiotic were carried out in BHI broth (Merck). An overnight of the target strain was subcultured and incubated to an OD600 nm of 0.5 before being diluted to give a final inoculum of $10^5$ cfu/ml in 200 µL and added to the antibiotic preparations. The plates were incubated at an appropriate temperature and inspected after 16 hours. The MIC was determined as the lowest concentration at which no growth was visible.

These results demonstrate that pharmaceutical compositions comprising the strains of the present technology alone or in combination with antibiotics, such as metronidazole, are useful in methods for treating or preventing *C. difficile* infections or CDAD.

Example 10: Freeze-Drying (Lyophilization) to Preserve the *B. amyloliquefaciens* Strains of the Present Technology This example demonstrates that the strains of the present technology are useful in compositions and methods wherein the strains are freeze-dried (or lyophilized).

2×SG Sporulation media: Difco nutrient broth 16.0 g/L; KCl, 2.0 g/L; $MgSO_4 \cdot 7H_2O$, 0.5 g/L. Adjust the pH to 7.0, autoclave. After autoclaving and cooling add 1 M $Ca(NO_3)_2 \cdot 4H_2O$, 1.0 ml/L; 0.1M $MnCl_2 \cdot 4H_2O$, 1.0 ml/L; 1 mM $FeSO_4 \cdot 7H_2O$, 1.0 ml/L; 50% (w/v) glucose, 2.0 ml/L.

Spore preparation method: Inoculate 50 ml of BHI (1.10493.0500, Merck) medium with cells from a fresh colony of *B. amyloliquefaciens*. Grow aerobically in flasks 24 hours at 37° C. with shaking (orbital platform shaker) at 200 rpm. Dilute 1/200 into 1 L 2×SG medium in an appropriate vessel and grow at 37° C. with shaking at 200 rpm. Check samples for spores daily using light microscopy. Phase contrast microscopy is ideal. After 2-3 days >90% of the population should have sporulated. Pellet cells at 9000 rpm for 20 minutes in a centrifuge if possible, keeping temperatures low, otherwise for small quantities a benchtop centrifuge will suffice. Wash and centrifuge the spores with ice-cold water 2-3 times to remove residual nutrients and lyse remaining vegetative cells. Resuspend the spore pellet in 10 mg/ml lysozyme solution and incubate shaking at 37° C. for 1 hour. Wash and centrifuge the spores with ice-cold water 4-6 times to remove residual nutrients and lyse remaining vegetative cells. Freeze dry 3 ml aliquots of spores over 24 hr period in a VirTis Advantage Wizard freeze dryer and store in sealed freeze-drying vials at room temperature for long-term storage.

Simulated gastric fluid was prepared based on the SGF outlined by the Infogest COST action containing 37.3 g/L KCl, 68 g/L $KH_2PO_4$, 84 g/L $NaHCO_3$, 117 g/L NaCl, 30.5 g/L $(NH_4)CO_3$, 44.1 g/L $CaCl_2$ and 2 mL of a 20,000 U/mL solution. As shown in FIG. 10A, spores of the *B. amyloliquefaciens* strains of the present technology (e.g., ART4, ART12, and ART24) survive when exposed to simulated gastric fluid.

Figure 10B:
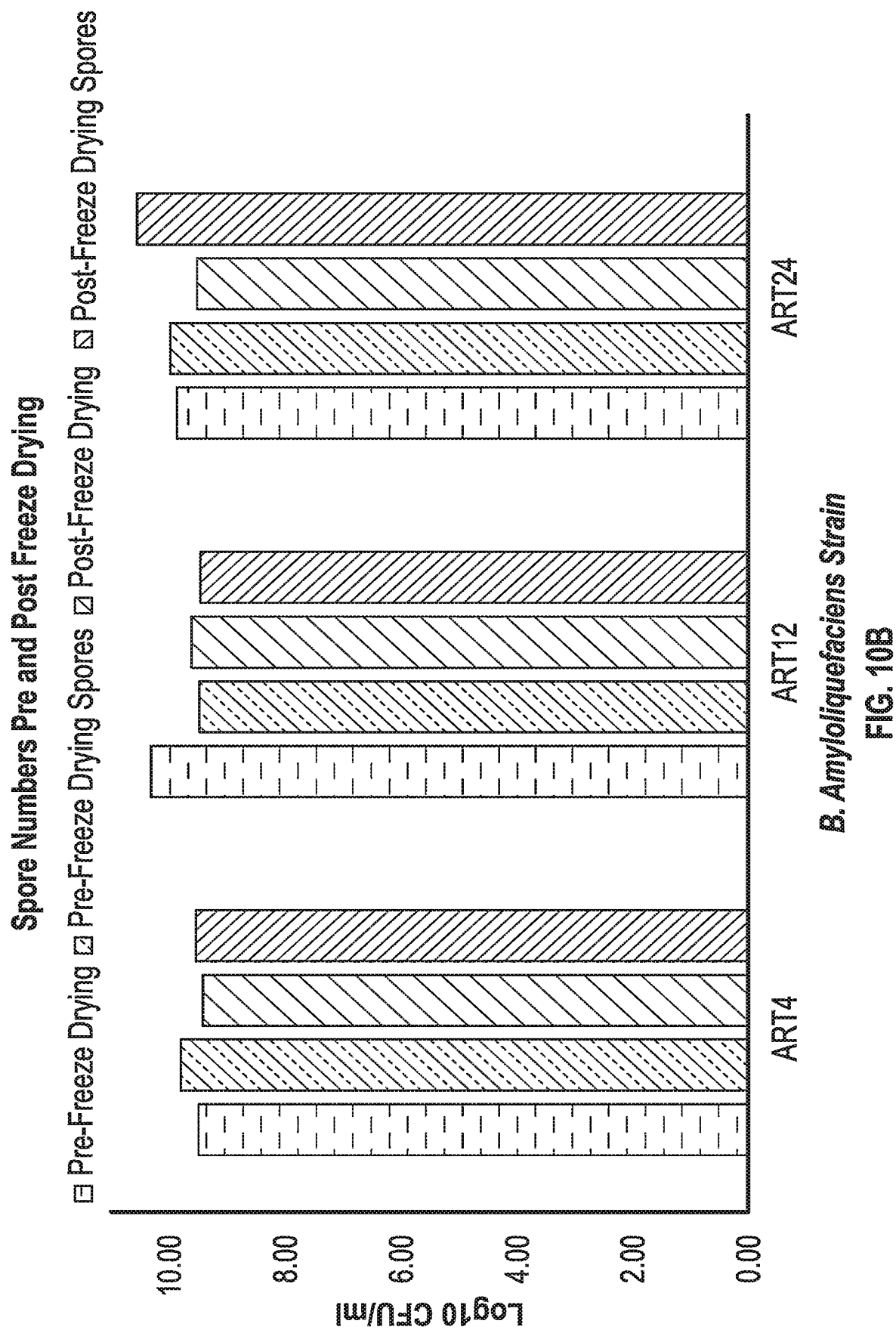
FIG. 10B is a chart showing the stability of ART4, ART12, and ART24 spores pre- and post-freeze drying (pre- and post-lypophilization).

As shown in FIG. 10B and Table 6, spores of the *B. amyloliquefaciens* strains of the present technology (e.g., ART4, ART12, and ART24) achieve 100% survivability after freeze drying and resuspension.

To test the robustness of the cells, the strains were freeze-dried. Briefly, overnight cultures of ART24, ART4, and ART12 were grown according to methods known in the art and re-suspended in 15% w/v trehalose solution. Cell counts were performed.

The cultures were freeze-dried for 22 hours, after which they were re-suspended in an equivalent volume of water lost. Cell counts were performed. Table 6 shows the survivability results.

TABLE 6

Survivability of *B. amyloliquefaciens* strains after freeze drying (lyophilization)

| | Pre FD (log) | Post FD (Log) |
|---|---|---|
| ART4 | 8.6 | 8.6 |
| ART12 | 8.5 | 8.7 |
| ART24 | 8.2 | 8.9 |

Accordingly, these results demonstrate that the strains of the present technology are useful in compositions and methods wherein the strains are freeze-dried (or lyophilized).

Example 11: Evaluation of In Vivo Efficacy

This example will demonstrate the in vivo efficacy of the *B. amyloliquefaciens* strain ART24 in methods for the treatment and prevention of *C. difficile* infections or CDAD.

Figure 8A:
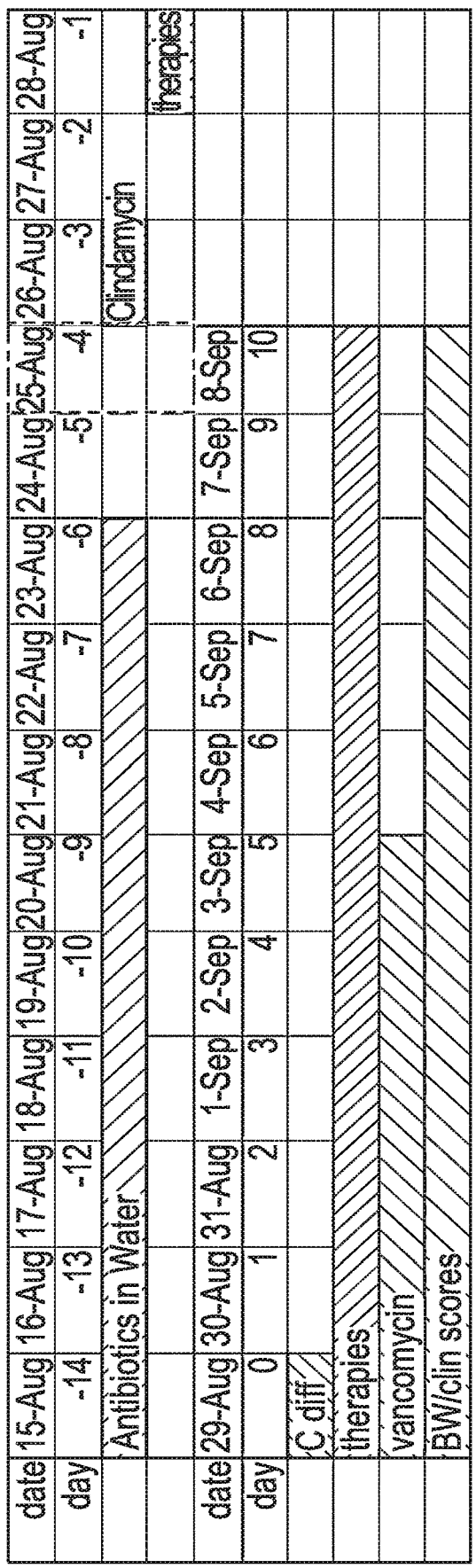

FIG. 8A provides an illustrative design for assessing the in vivo efficacy of the *B. amyloliquefaciens* ("B. amy") strains of the present technology. Table 7 provides a description of the groups used in the study described below.

TABLE 7

General design of in vivo studies

| Group | n | treatment (day −1 to 10; QD, PO) |
|---|---|---|
| 1 | 15 | vehicle (PBS) |
| 2 | 15 | B amy in culture medium* |
| 3 | 15 | B amy in PBS# |
| 4 | 15 | Vancomycin (day 0-5) |

*B amy culture centrifuged and resuspended in the spent culture medium
B amy culture centrifuged, removed as much supernatant as possible, resuspended in PBS
B amy is grown fresh daily

*C. difficile* mouse model. The mouse model of *C. difficile* infection was prepared as described elsewhere (Chen, X, et al., *Gastroenterology* 135:1984-1992 (2008)).

Mice (C57BL/6J female) were divided prospectively into 4 treatment groups of 15 animals (Table 7) and housed 5 animals per cage.

Mice received an antibiotic cocktail for eight consecutive days in their drinking water starting 13 days prior to *C. difficile* infection (study day 0). The antibiotic cocktail was changed every third day with freshly prepared antibiotics provided. The antibiotic cocktail consisted of 1% glucose, kanamycin (0.5 mg/mL), gentamicin (0.044 mg/mL), colistin (1062.5 U/mL), metronidazole (0.269 mg/mL), ciprofloxacin (0.156 mg/mL), ampicillin (0.1 mg/mL) and vancomycin (0.056 mg/mL). Five days prior to *C. difficile* infection, the antibiotic water was removed. Animals were placed in clean cages and sterile drinking water provided to the mice. Three days prior to infection mice were administered Clindamycin at 10 mg/kg via oral gavage in a volume of 10 mL/kg.

Test article preparation. *B. amyloliquefaciens* was cultured in vitro in preparation for in vivo testing and stored as −80° C. glycerol stocks.

The strain was applied to TSA agar plates from frozen stocks (3 days prior to dosing) and cultured overnight at 37° C. From the overnight plate culture, a colony was resuspended in 50 mL of BHI broth and incubated overnight at 37° C. while shaking. The overnight culture was diluted 1:100 in fresh BHI broth (100 mL) and incubated for 16 hours at 37° C. while shaking. The culture was then centrifuged at 2,500 RPM for 20 minutes. The supernatant was removed and the pellet was resuspended in either a total of 10 mL of the spent medium, or a total of 10 mL of sterile PBS. Serial dilutions of the prepared suspension and plating on TSA agar was performed each day of dosing to confirm inoculum concentration.

*C. difficile* preparation. Four days prior to infection, *C. difficile* ATCC 43255 was cultured from a frozen stock applied to TSA-II plates and incubated anaerobically for 48 hours at 37° C. After 48 hours, colonies from the plate were resuspended in SMB (sporulation media broth) and adjusted to an OD of 0.2 at 600 nm wave length. The adjusted bacterial suspension was diluted 1:10 into fresh SM broth and incubated anaerobically for 48 hours at 37° C. After 48 hours of incubation, the bacterial suspension was adjusted to an OD of 0.2 and subsequently diluted 100-fold into saline to generate the infecting inoculum. Serial dilutions of the inoculum were performed to determine the actual CFU input. A spore preparation of the inoculum was also performed to determine the ratio of spores to vegetative cells in the inoculum.

Infection establishment. All sixty mice were infected with 0.20 mL of the prepared *C. difficile* bacterial suspension via oral administration. The animals were returned to their cages after the infection. The inoculum was delivered to the animals on day zero of the study, approximately 4 hours after the animals received the day 0 *B. amyloliquefaciens* treatment.

Test article (*B. amyloliquefaciens*) treatment. Animals began receiving treatment of either the *B. amyloliquefaciens* cells resuspended in spent medium ("B amy QD") or resuspended in PBS ("B amy PBS") one day prior to infection. All animals were dosed via oral gavage in a volume of 0.2 mL/mouse. Control mice received vancomycin at 50 mg/kg and a dose rate of 10 mL/kg. Dosing materials were prepared fresh daily as described above in test material preparation.

Observations. Mice were observed daily through the course of the study. Body weights were collected beginning with Day −1 and continuing until study termination (Day 10). Clinical observations were also performed with adverse observations recorded when appropriate. Observations included absence/presence of diarrhea (wet tail), lethargy, hunched posture, abnormal temperature (cold to the touch), fur condition, dehydration, and death.

Figure 8B:
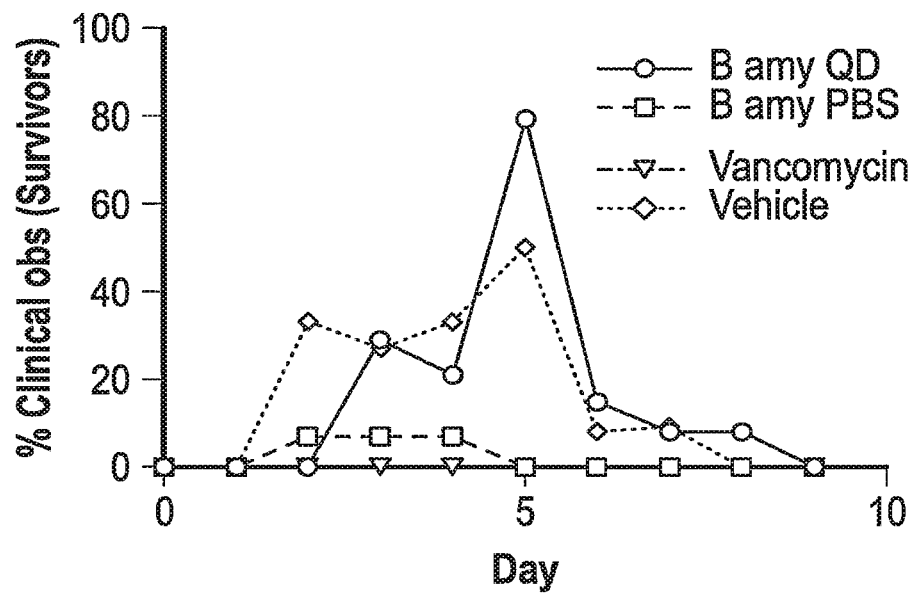

Results. As shown in FIG. 8B mice dosed once per day with ART24 cells resuspended in PBS ("B amy PBS") exhibited a much lower percentage of abnormal clinical signs as compared with the "vehicle" (PBS) dosed group. This was a similar percentage as that of the vancomycin-treated group.

Figure 8C:
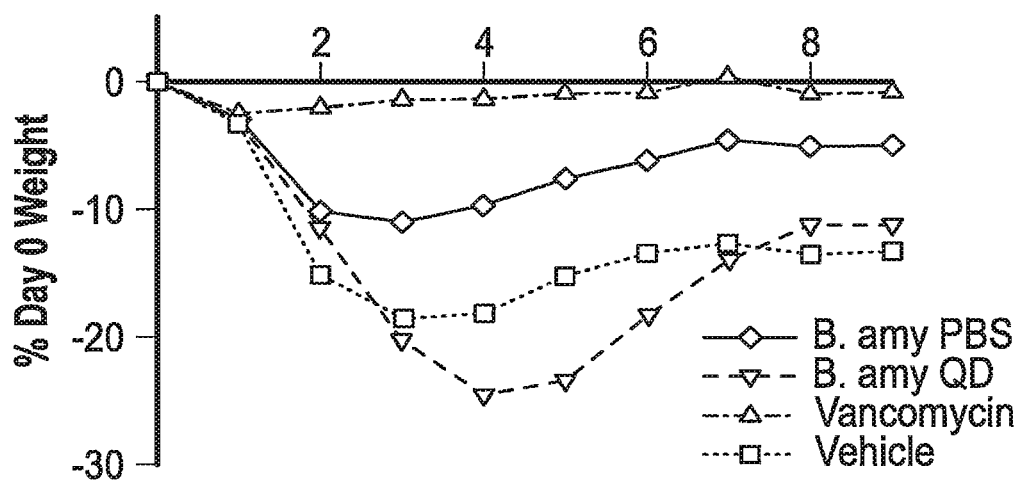

As shown in FIG. 8C treatment of *C. difficile*-infected mice with ART24 cells resuspended in PBS ("B. amy PBS") but not spent medium ("B. amy QD") reduces *C. difficile* infection-induced weight loss as compared with the vehicle-treated group.

Figure 8D:
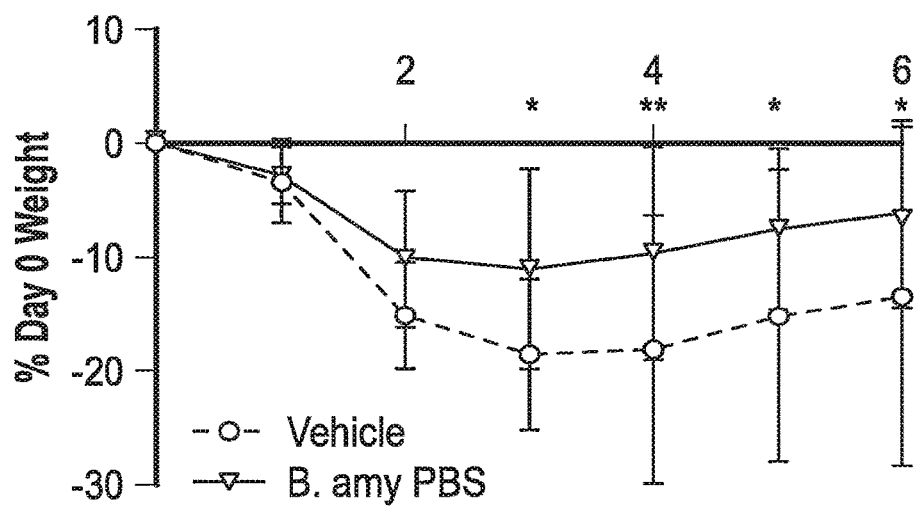

FIG. 8D shows the average weights of animals in the B. amy PBS dose group and per day statistical analysis. $*p<0.05$; $**p<0.01$; 2-way ANOVA with multiple comparisons.

Figure 8E:
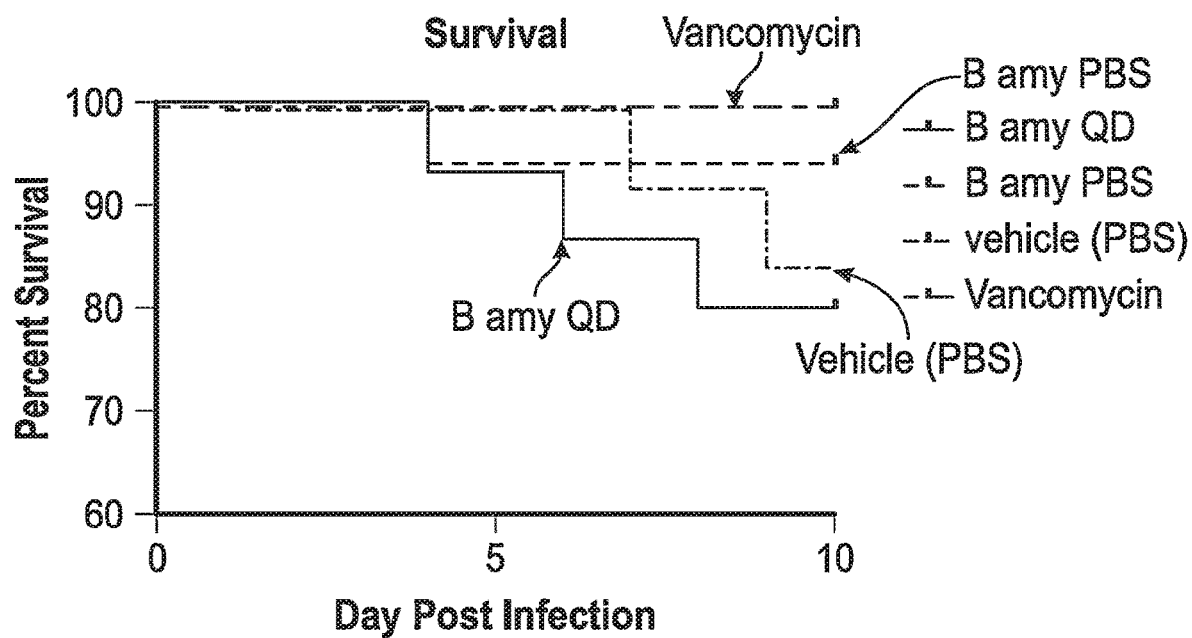

As shown in FIG. 8E, more animals survived in the B amy PBS-dosed group (14/15) and vancomycin-treated group (15/15) than the vehicle-treated group (11/15) or the group dosed with *B. amyloliquefaciens* resuspended in spent medium ("B amy QD"; 12/15).

Accordingly, these results demonstrate that the *B. amyloliquefaciens* strains of the present technology are useful in methods for treating and preventing *C. difficile* infections or CDAD.

Example 12: *Bacillus amyloliquefaciens* Strains Exhibit Anti-*C. perfringens* and Anti-*L. monocytogenes* Activity This example demonstrates that *B. amyloliquefaciens* strains of the present technology exhibit anti-*C. perfringens* and anti-*L. monocytogenes* activity.

ART4, ART12, and ART24 strains were grown in BHI broth aerobically, shaking at 200 rpm and incubated at 37° C. Overnight cultures of the bacterial strains were centrifuged and the supernatants pH neutralized and filter sterilized with 0.22 μm filters to ensure cell free supernatants (CFS). Fifty microlitres of the bacterial CFS were dispensed into the wells of the RCM plate anaerobically and the plate was allowed to incubate for 24 h. Anti-*C. perfringens* and *L. monocytogenes* activity was assessed by examining the presence or absence of zones of inhibition surrounding the wells.

Figure 9A:
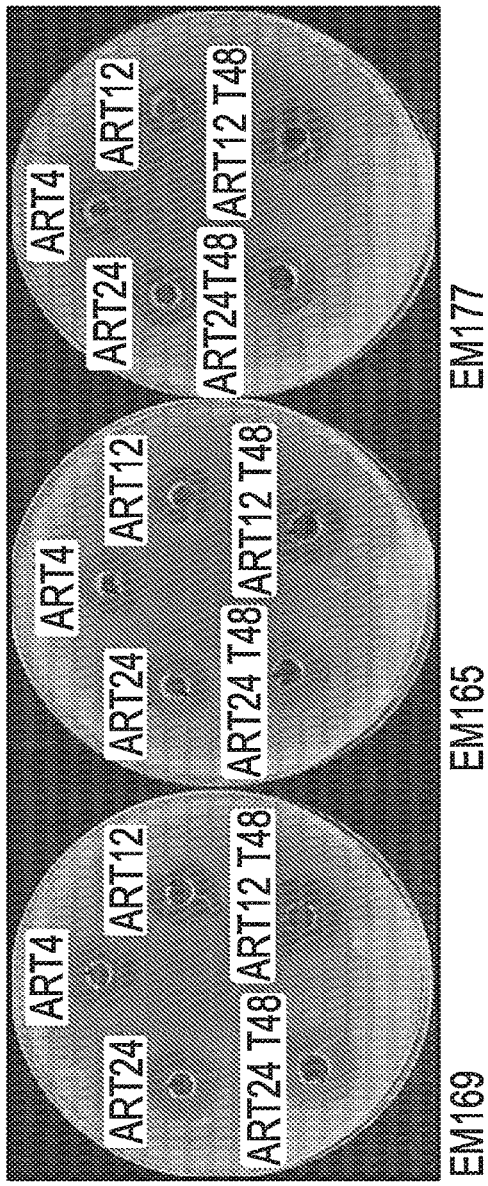
FIG. 9F shows an anti-*L. monocytogenes* well diffusion assay demonstrating the inhibitory effects of ART4, ART12, and ART24 against a single strain of *Listeria monocytogenes*.
Figure 9A:
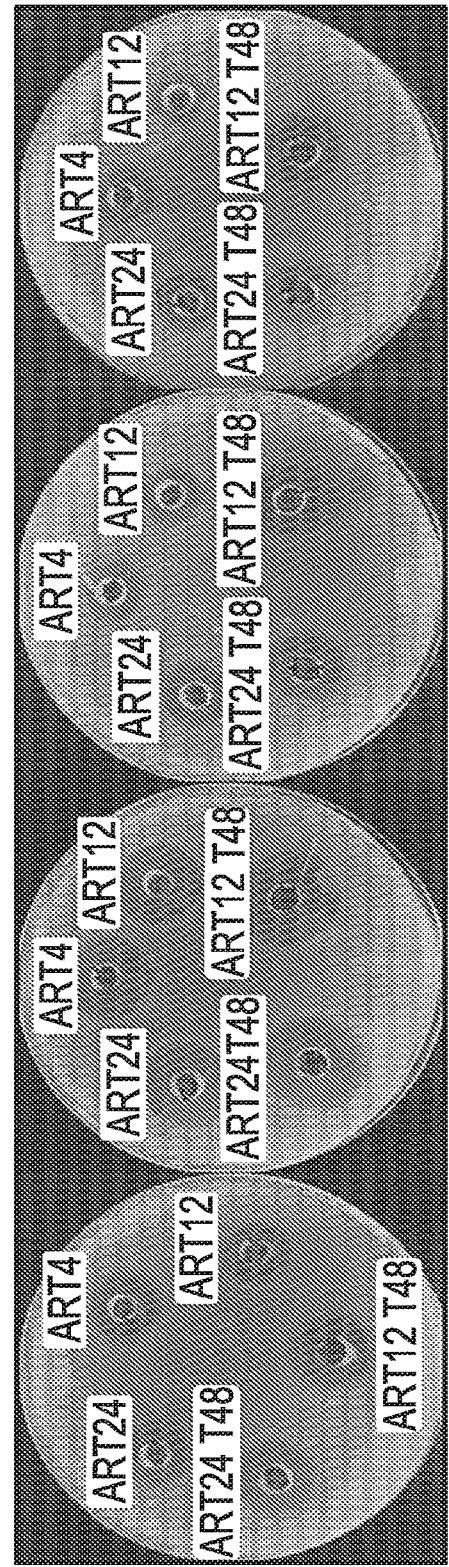
Figure 9B:
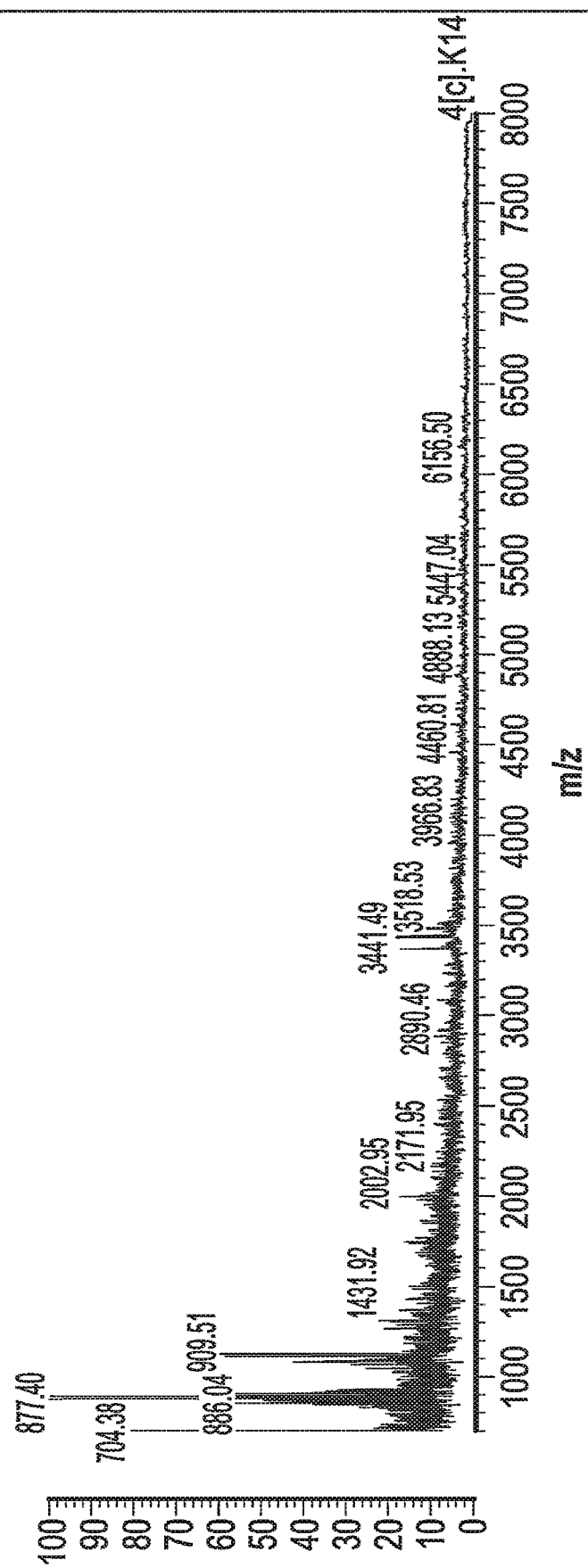
Figure 9C:
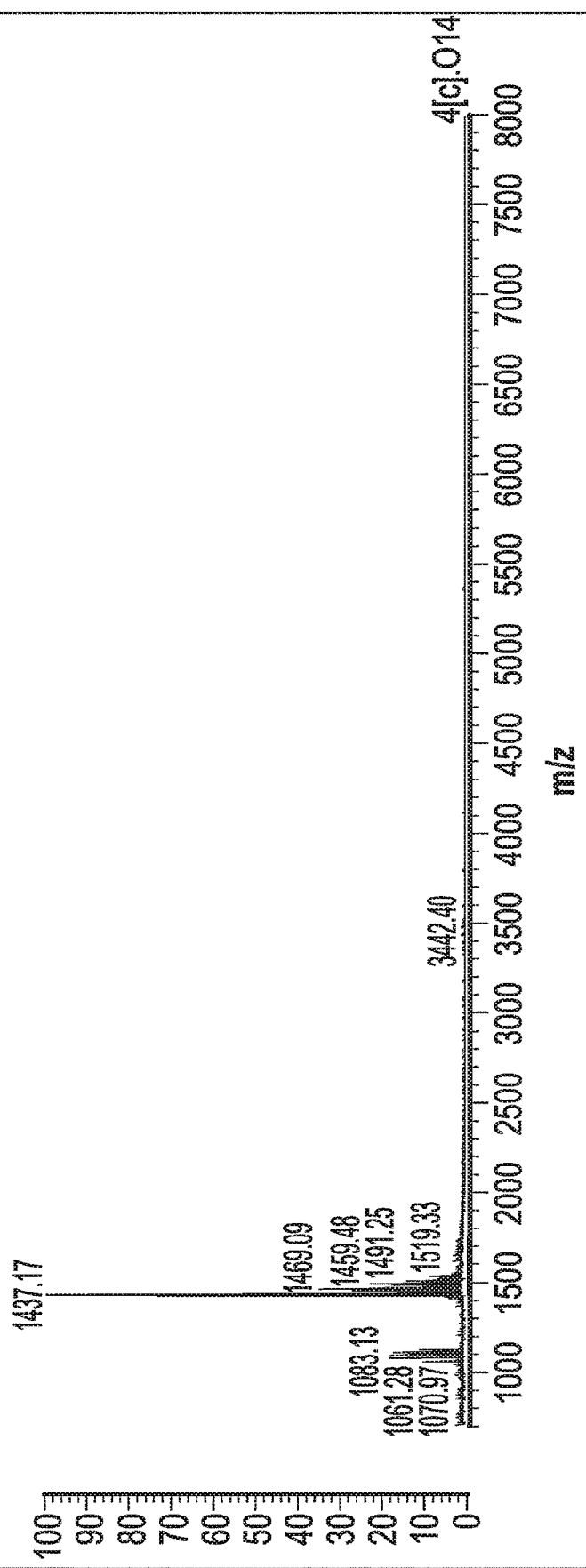
Figure 9D:
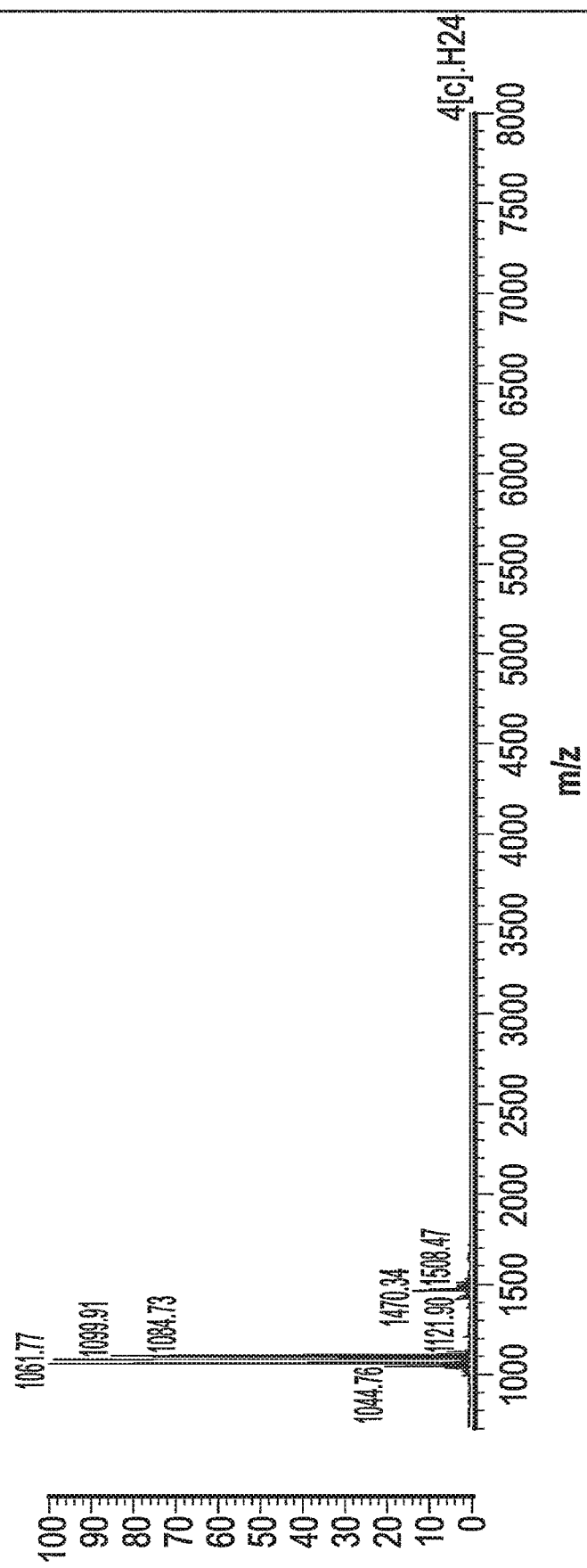
Figure 9E:
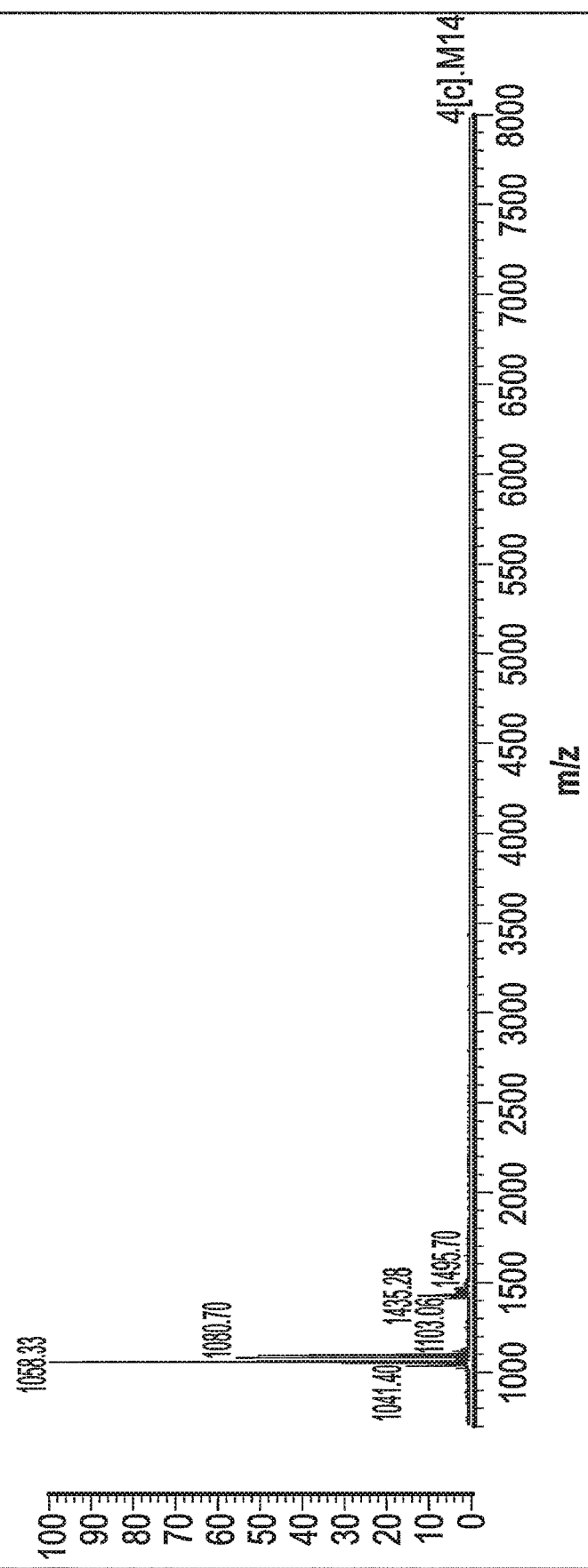

Using the WDA method described above, the prepared supernatants of each of the three candidates, ART24, ART4, ART12, were tested against 7 clinical isolates of *C. perfringens*. FIG. 9A shows the zones of activity achieved against *C. perfringens*.

As shown in FIGS. 9B-9E, MALDI-TOF MS chromatographs of HPLC fractions of culture DSM7$^T$ (FIG. 9B), ART4 (FIG. 9C), ART12 (FIG. 9D), and ART24 (FIG. 9E) against *C. perfringens* indicate plipastatin (fengycin) as the active anti-*C. perfringens* metabolite. Plipastatin is not present on spectrum from fractions of DSM7$^T$ (FIG. 9B) culture supernatant.

Figure 9F:
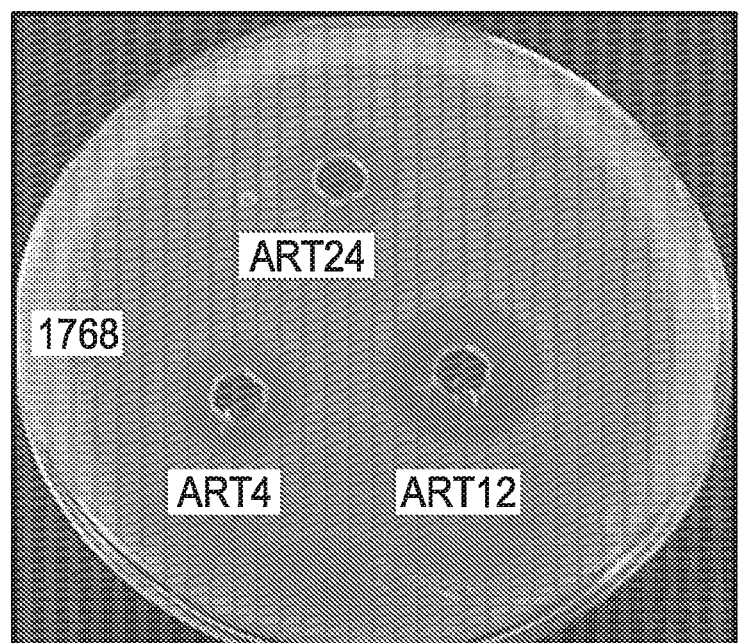

As shown in FIG. 9F, an anti-*L. monocytogenes* well diffusion assay demonstrates the inhibitory effects of ART4, ART12, and ART24 against a single strain of *L. monocytogenes*.

Accordingly, these results show that the *B. amyloliquefaciens* strains of the present technology are useful in methods of inhibiting *C. perfringens* and *L. monocytogenes* growth and are useful in methods for treating and preventing *C. perfringens* and *L. monocytogenes* infections.

Example 13: Lyophilized *Bacillus amyloliquefaciens* Strains Exhibit Anti-*C. difficile* Enterotoxin (Toxin A) and Cytotoxin (Toxin B) Activity and are Cidal to *C. difficile* in Liquid Co-Culture Assay Activity Against Toxins A and B Freshly grown ART24 in Brain Heart Infusion (BHI) media as well as the pelleted cell portion, prepared as an isopropanol (IPA)-extracted supernatant fraction and ART24 lyophilized powder (Drug substance lot CO-33-8A1) reconstituted in PBS were examined for *C. difficile* toxins A and B cleavage activity. Western blot analysis was conducted using standardized toxin A and B antibodies.

Figure 11A:
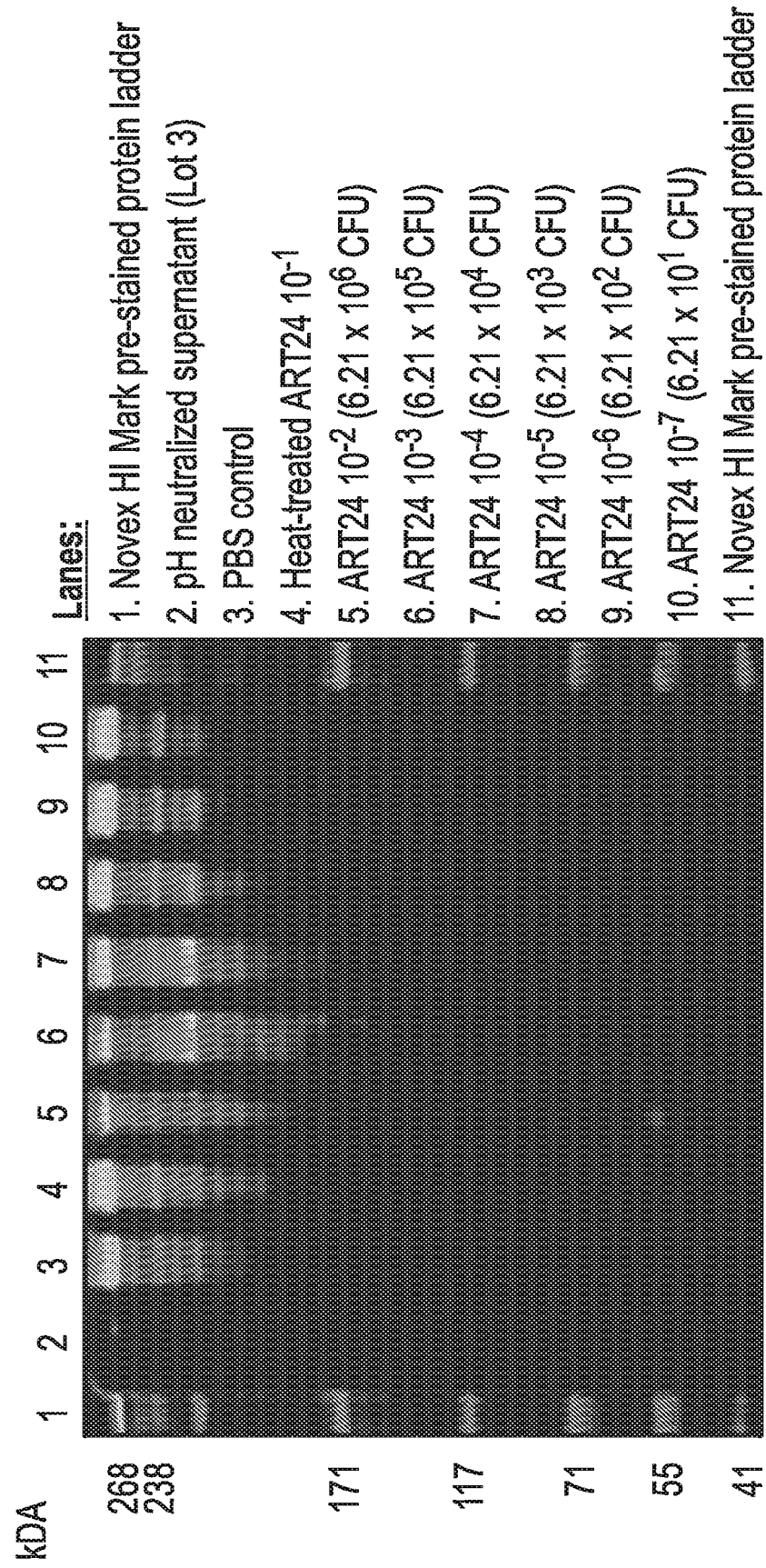
FIG. 11A is a Western blot showing the cleavage detection of *C. difficile* toxin A by reconstituted lyophilized ART24 (lot CO-33-8A1).
Figure 11B:
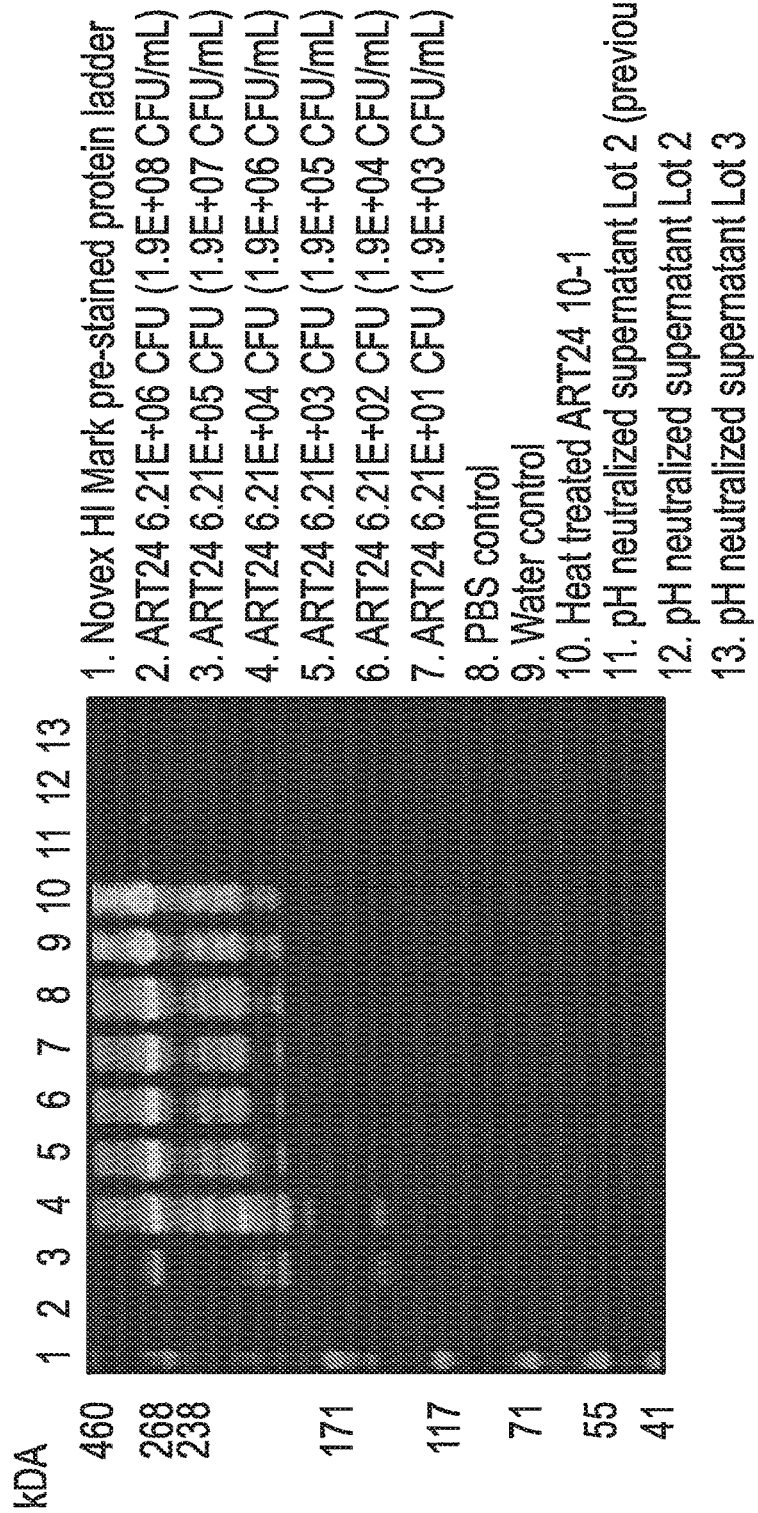
FIG. 11B is a Western blot showing the cleavage detection of *C. difficile* toxin B by reconstituted lyophilized ART24 (lot CO-33-8A1).

It was observed that pH-neutralized, IPA-extracted supernatants from freshly grown ART24 and reconstituted lyophilized ART24 preparation caused complete cleavage of *C. difficile* toxin A (FIG. 11A) and toxin B (FIG. 11B). The amount of toxin cleavage was dependent upon the amount of lyophilized ART24 CFUs reconstituted.

Liquid Co-Culture Assay

A preparation of lyophilized ART24 was added in a liquid culture comprising a mixture of *C. difficile* vegetative cells or *C. difficile* spores and incubated in BHI media supplemented with sodium taurocholate as a liquid co-culture for 24 hours. The ART24 was present at $1\times10^7$ CFU/mL and *C. difficile* was present at $1\times10^3$ CFU/mL. Baseline counts were performed in duplicate and counts at 24 hours were performed in triplicate.

Figure 11C:
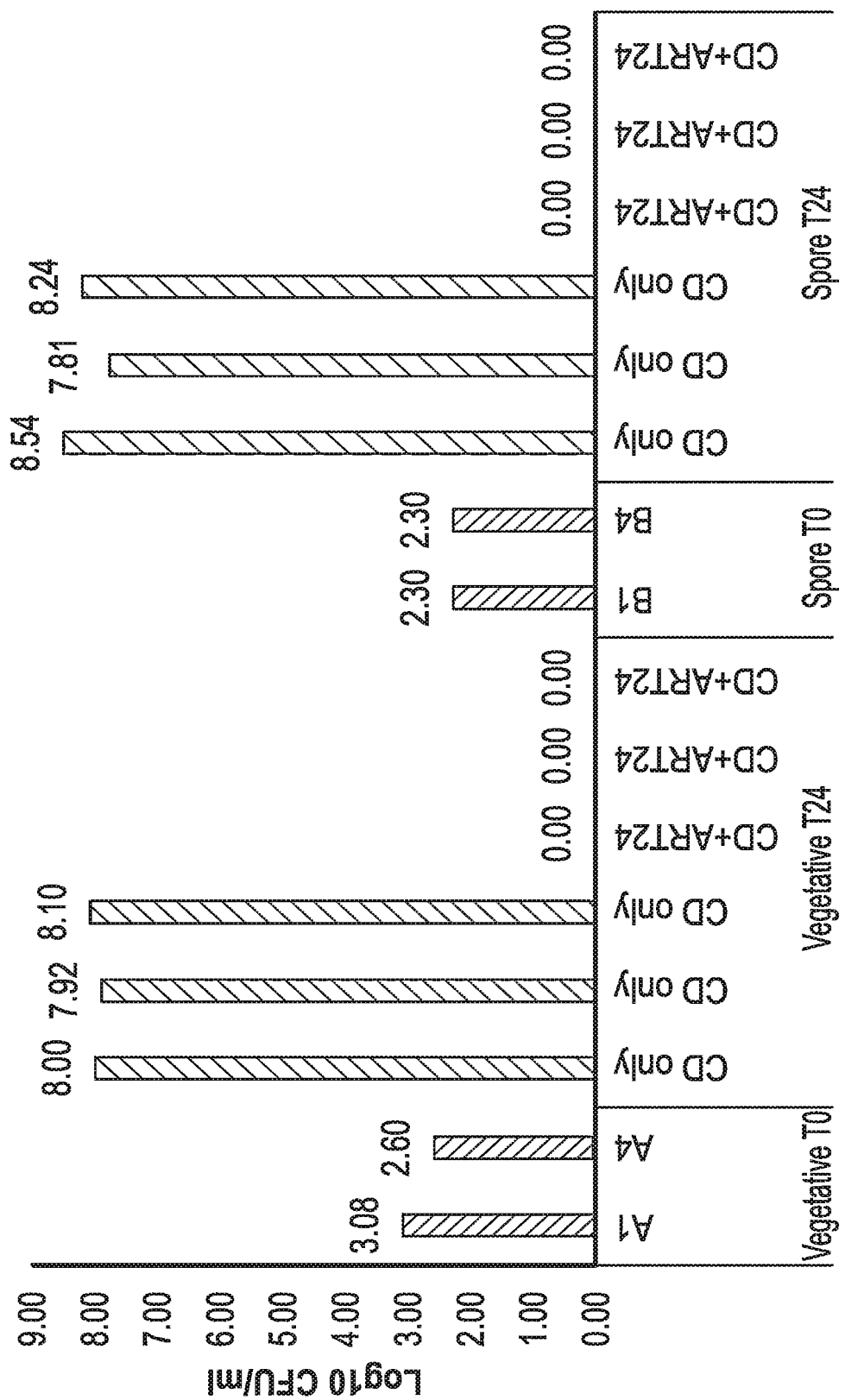
FIG. 11C is a chart showing anti-*C. difficile* activity of $1×10^7$ CFU ART24 on *C. difficile* spores and vegetative cell counts in liquid co-culture.

As shown in FIG. 11C, after 24 hours, the *C. difficile* sample cultured in the absence of ART24 showed a >4 log increase in *C. difficile* CFU/mL when compared to the count at the start of the culture. In contrast, the cultures inoculated with ART24 showed a >2 log reduction in *C. difficile* counts, below the limit of detection of the assay. *C. difficile* vegetative and spore counts were not quantifiable/detectable in samples containing ART24.

Overall, these results demonstrate that the *B. amyloliquefaciens* strains of the present technology retain their anti-*C. difficile* activity even after processing (e.g., washing, centrifugation, mixing with trehalose/cryoprotectant) and lyophilization. These results also demonstrate that the anti-*C. difficile* activity is present after rehydration of lyophilized material. Accordingly, these results demonstrate that lyophilized *B. amyloliquefaciens* strains of the present technology are useful in methods for treating or preventing *C. difficile* infections or CDAD.

Example 14: The *B. amyloliquefaciens* Strains of the Present Technology Demonstrate Activity Against *Vibrio parahaemolyticus*

Figure 12:
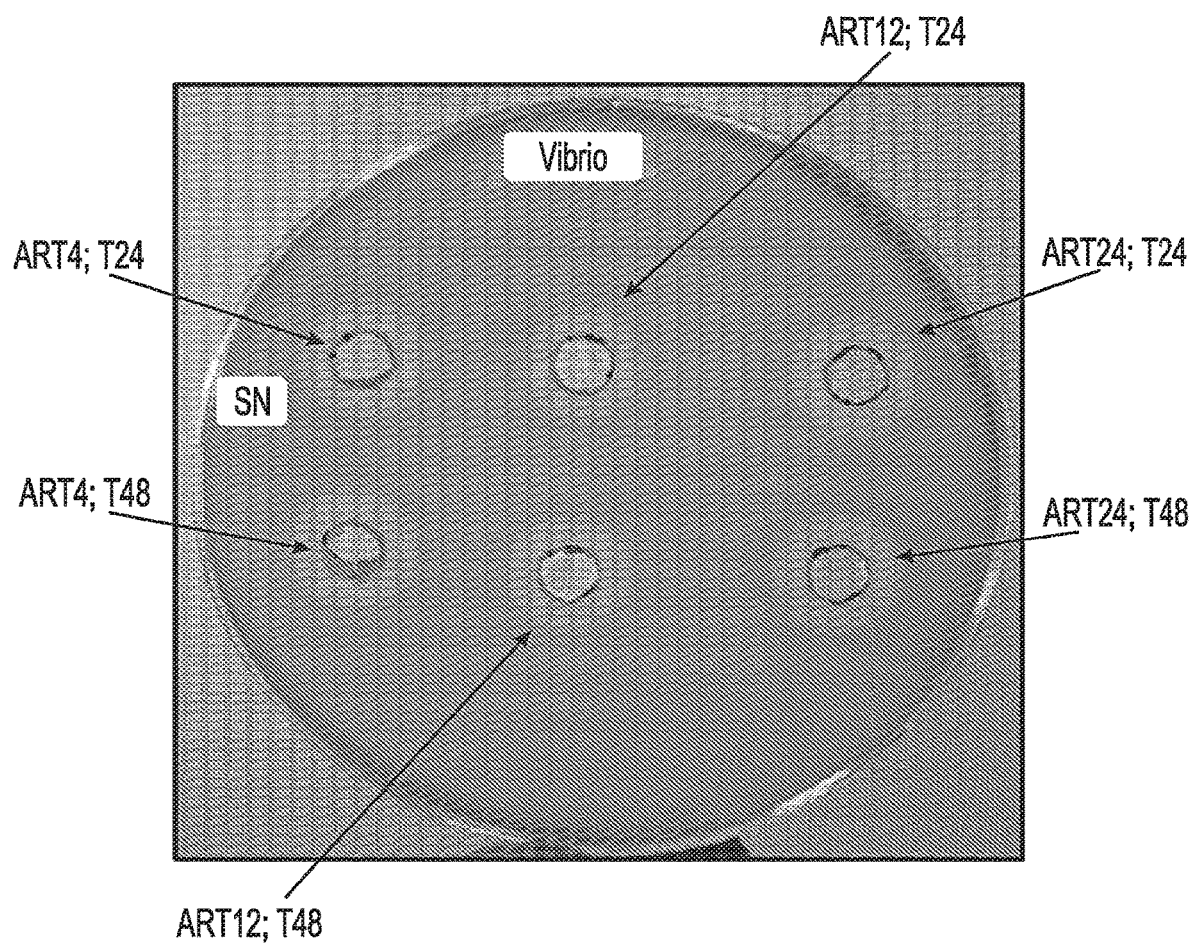
FIG. 12 is a well-diffusion assay showing zones of anti-*V. parahaemolyticus* activity for each of the culture supernatants from strains ART4, ART12, and ART24.

This example demonstrates that *B. amyloliquefaciens* strains of the present technology exhibit anti-*Vibrio parahaemolyticus* activity (FIG. 12).

The antimicrobial activity of ART4, ART12, and ART24 were tested against *V. parahaemolyticus* DSM 10027 (ATCC 17802, CIP 75.2, NCMB 1902, NCTC 10903, WDCM 00037). *V. parahaemolyticus* was grown in LB+3% salt liquid media shaking at 170 rpm overnight in a flask at 37° C. and then added as a 1% inoculum to tempered LB+3% salt agar. The plates of LB+3% agar were allowed to cool, and once cool, the wells were made in the agar using pipettes. Time 24 hours (T24) and time 48 hours (T48) cell free supernatants of ART4, ART12, and ART24 were added to the wells and the plates were incubated at 37° C. and then examined for zone formation.

A well-diffusion assay shown in FIG. 12 shows zones of anti-*V. parahaemolyticus* activity for each of the culture supernatants from strains ART4, ART12, and ART24.

Accordingly, these results show that the *B. amyloliquefaciens* strains of the present technology are useful in methods of inhibiting *V. parahaemolyticus* growth and are useful in methods for treating *V. parahaemolyticus* infection.

What is claimed is:

1. A method of preparing a therapeutic composition, comprising, combining one or more bacterial strains selected from the group consisting of ART24 (NCIMB Accession No. 43088), ART4 (NCIMB Accession No. 43086), and ART12 (NCIMB Accession No. 43087) With a preservative.

2. The method of claim 1, wherein the bacterial strain is ART24 (NCIMB Accession No. 43088).

3. The method of claim 1, wherein the bacterial strain is ART4 (NCIMB Accession No. 43086).

4. The method of claim 1, wherein the bacterial strain is ART 12 (NCIMB Accession No. 43087).

5. The method of claim 1, wherein the preservative is selected from the group consisting of sucrose, trehalose, sodium ascorbate, and glutathione.

6. The method of claim 1, wherein the preservative is a cryoprotectant.

7. The method of claim 6, wherein the cryoprotectant is selected from the group consisting of a nucleotide, a disaccharide, a polyol, and a polysaccharide.

8. The method of claim 6, wherein the cryoprotectant is selected from the group consisting of inosine-5'-monophosphate (IMP), guanosine-5'-monophosphate (GMP), adenosine-5'-monophosphate (AMP), uranosine-5'-monophosphate (UMP), cytidine-5'-monophosphate (CMP), adenine, guanine, uracil, cytosine, guanosine, uridine, cytidine, hypoxanthine, xanthine, orotidine, thymidine, inosine, trehalose, maltose, lactose, sucrose, sorbitol, mannitol, dextrin, inulin, sodium ascorbate, glutathione, and skim milk.

9. The method of claim 8, wherein the cryoprotectant comprises trehalose.

10. The method of claim 1, wherein the one or more bacterial strains are in spore form.

11. The method of claim 10, wherein the one or more bacterial strains are sporulated using nutrient exhaustion media.

12. The method of claim 10, wherein the one or more sporulated bacterial strains exhibit acid tolerance.

13. The method of claim 12, wherein the one or more sporulated bacterial strains exhibit gastric fluid tolerance.

14. The method of claim 1, wherein the one or more bacterial strains are lyophilized.

15. The method of claim 14, wherein the one or more lyophilized bacterial strains are resuspended in a solution containing the preservative.

\* \* \* \* \*